US005229112A

United States Patent [19]
Obukowicz et al.

[11] Patent Number: 5,229,112
[45] Date of Patent: Jul. 20, 1993

[54] **COMBATTING PLANT INSECT PESTS WITH PLANT-COLONIZING MICROORGANISMS CONTAINING THE TOXIN GENE *B. THURINGIENSIS* AS A CHROMOSOMAL INSERTION**

[75] Inventors: Mark G. Obukowicz, Olivette; Frederick J. Perlak, St. Louis; Lidia S. Watrud, Maryland Heights, all of Mo.

[73] Assignee: Monsanto Company, St. Louis, Mo.

[21] Appl. No.: 363,318

[22] Filed: Jun. 7, 1989

Related U.S. Application Data

[63] Continuation of Ser. No. 799,369, Nov. 18, 1985, abandoned, which is a continuation-in-part of Ser. No. 728,906, Apr. 30, 1985, abandoned.

[51] Int. Cl.$^5$ .............................................. A01N 63/00
[52] U.S. Cl. ................................ 424/93 A; 435/252.3; 435/252.34
[58] Field of Search ................... 424/92, 93, 88, 93 A; 514/2; 435/69.1, 91, 172.3, 170, 252.3, 320.1, 822, 824; 935/6, 9, 22, 29, 59, 60, 64, 66, 72

[56] References Cited

U.S. PATENT DOCUMENTS

| | | | |
|---|---|---|---|
| 4,277,564 | 7/1981 | Johnson | 435/242 |
| 4,374,200 | 2/1983 | Olsen | 435/172.3 |
| 4,448,885 | 5/1984 | Schnepf et al. | 435/252.33 |
| 4,536,475 | 8/1985 | Anderson | 435/172.3 |
| 4,695,455 | 9/1987 | Barnes et al. | 424/93 |

FOREIGN PATENT DOCUMENTS

| | | |
|---|---|---|
| 127328 | 12/1984 | European Pat. Off. |
| 130047 | 1/1985 | European Pat. Off. |
| 192319 | 8/1986 | European Pat. Off. |
| 213818 | 3/1989 | European Pat. Off. |
| WO8601536 | 3/1986 | PCT Int'l Appl. |

OTHER PUBLICATIONS

L. Watrud et al., in Engineered Organisms in the Environment, American Society for Microbiology, Washington, 1985, pp. 40–46.
Chemical Abstracts, 105:220216b (1986) [Obukowicz et al., *J. Bacteriol.* 1986, 168, 982–9).
R. McClure, *Ann. Rev. Biochem.* 1985, 54: 171–204.
T. Kunkel, *PNAS (USA)*, 82, 488–492 (1985).
D. Shortle et al., *Ann. Rev. Genet.* 1981, 15: 265–294.
Kennell, 1985, In: Maximizing Gene Expression, W. Reznikoff and L. Gold (eds.), Butterworth Press, Boston, pp. 101–142.
Goldberg et al., 1985, In: Maximizing Gene Expression, W. Reznikoff and L. Gold (eds.), Butterworth Press, Boston, pp. 287–314.
Cullen et al., 1986, TIBTECH, pp. 115–119.
Lindow, S. E., In: Microbiology of the Phyllosphere, Fokkema et al. (eds) Cambridge Univ. Press, Cambridge, pp. 293–311 (1986).
Panopoulos, N. J., 1986, In: Microbiology of the Phyllosphere, Fokkema et al (eds.), Cambridge Univ. Press, Cambridge, pp. 312–334.
Kloepper et al., 1981, Phytopathology, vol. 71: 590–592.
McKay et al., 1978, Applied and Environmental Microbiology, vol. 36: 360–367.

(List continued on next page.)

Primary Examiner—Richard A. Schwartz
Attorney, Agent, or Firm—Larry R. Swaney

[57] ABSTRACT

The invention relates to a plant-colonizing microorganism which has been genetically engineered to integrate into the chromosome of such microorganism, DNA derived from *B. thuringiensis* coding for protein toxin. The genetically engineered plant-colonizing microorganisms of the invention, and their progeny, proliferate in commensal or non-detrimental relationship with the plant in the plant environment and are insecticidally active against a subspecies of insect pest which are harmful to the plant. The invention further relates to insecticidal compositions containing such plant-colonizing microorganisms as the active insecticidal agent and to a method of using such genetically engineered plant-colonizing microorganisms in a method of killing or inhibiting insect pests.

32 Claims, 3 Drawing Sheets

OTHER PUBLICATIONS

Simon et al., Bio/Technology, vol. 1, 784–791 (1983).
Held et al. 1982, *PNAS* 79: 6065–6069.
Dean, D. H. 1984, In: Biotechnology and Genetic Engineering Reviews 2: 341–363.
Weller, D. H. 1984 *Appl. Environ. Microbiol.* 48(4): 897–899.
Bagdasarian et al. 1981 *Gene* 16: 237–247.
Schnepf et al. 1981, *PNAS* 78(5): 2893–2897.
Klier et al., (1982) *EMBO J.* 1, pp. 791–799. "Cloning and Expression of the Crystal Protein Genes from *Bacillus thuringiensis* strain berliner 1/15".
Held et al., (1982) *Microbiology*, 79, 6065–6069. "Cloning and localization of the lepidopteran protoxin gene of *Bacillus thuringiensis* subsp. kurstaki".
Wong et al., (1983) *J. Biol. Chem.*, 258, 1960–1967. "Transcriptional and Translational Start Sites for the *Bacillus thuringiensis* Crystal Protein Gene".
Faust et al., *Genetic Engineering in the Plant Sciences*, pp. 225–253, Praeger Publishers, New York, (1981).

| Recombinant Plasmid | Restriction Sites of Inserted B.t. Fragment | Fragment Size (Kb) |
|---|---|---|
| pMAP2 | BamHI  HpaI  PstI  BamHI | 16 |
| pMAP3 | HpaI  PstI  BamHI | 8.1 |
| pMAP4 | HpaI  PstI | 4.6 |

Figure 1

| Recombinant Plasmid | Restriction Sites of B.t. Fragment | Fragment Size (Kb) |
|---|---|---|
| pMAP8 | B   H   K   H   K   B<br>───────────────<br>           N   S | 4.6 |
| pMAP10 |    2.4Kb      1.5Kb<br>B           K               K       B<br>──────── - - - - ──────── | 3.1 |
| pMAP11 |    3.0Kb      .5Kb<br>B                       N   S   B<br>──────────── - - ──────── | 4.1 |

B = BamHI
H = Hind III
K = Kpn I
N = Nru I
S = ScaI

COMBATTING PLANT INSECT PESTS WITH PLANT-COLONIZING MICROORGANISMS CONTAINING THE TOXIN GENE B. THURINGIENSIS AS A CHROMOSOMAL INSERTION

This is a continuation of application Ser. No. 06/799,369, filed Nov. 18, 1985, which is a continuation-in-part of application Ser. No. 728,906 filed Apr. 30, 1985, now abandoned.

BACKGROUND OF THE INVENTION

The present invention is directed to a plant-colonizing microorganism, which contains as a chromosomal insert, heterologous DNA coding for a high molecular weight protein having insecticidal activity. The invention is further directed to insecticidal compositions containing such plant-colonizing microorganisms as the active insecticidal agent as well as to the use of such microorganisms in a method of combatting insect pests.

*Bacillus thuringiensis* (B.t.) subsp. kurstaki is a spore forming soil bacterium which is known for its ability to produce a parasporal crystal which is lethal to a wide subspecies of insect larvae. The crystals, which account for 20-30% of the dry weight of sporulated cultures, are composed primarily of a single, high molecular weight protein (134,000 daltons) which is synthesized only during sporulation.

Whiteley et al (1) reported the isolation of plasmid DNA from *Bacillus thuringiensis* subsp. kurstaki HD-1, insertion of said DNA into the cloning vector pBR322 and transformation into *Escherichia coli* strain HB101. Colonies presumed to contain recombinant plasmids were screened for production of an antigen that would react with an antibody made against B.t. crystal protein toxin. One recombinant strain, identified as ES12, was isolated which synthesized a polypeptide of 130,000 daltons which reacted with antibody directed to the crystal protein. Protein extracts of ES12 were toxic to larvae of the tobacco hornworm, *Manduca sexta*. The amounts of polypeptide produced were very low compared to that produced by *B. thuringiensis*. This appears to be due to the different methods of regulation of protein production in *B. thuringiensis* and *E. coli*.

Klier et al (2) reported that the crystal protein gene of *Bacillus thuringiensis* subsp. berliner 1715 occurred on both a large host plasmid and on the chromosomal DNA. A DNA sequence corresponding to the chromosomal sequence was inserted into plasmid pBT 15-88. The inserted sequence of pBT 15-88 was not expressed in *E. coli*. A 14 Kb BamHI DNA fragment from the 42 megadalton host plasmid was cloned into the BamHI site of pHV33 and this vector was inserted into *E. coli*. Extracts of *E. coli* containing the recombinant plasmid were immunologically cross-reactive against antibodies directed against purified crystal protein. The polypeptide synthesized by *E. coli* containing the recombinant plasmid had approximately 10% the activity of that synthesized by sporulating cells of *B. thuringiensis*. Five-fold concentrated extract of *E. coli* harboring the recombinant plasmid when spread on cabbage leaves and fed ad libitum were toxic to the larvae of *Pierris brassica*. Klier et al also inserted pHV33 containing the 14 Kb insert into *B. subtilis*. The crystal gene was not expressed in vegetative cells; it was expressed in sporulating cells although the amount of crystal protein produced by the sporulating cells was about 10% of that produced by sporulating *B. thuringiensis*.

Held et al (3) containing DNA fragments of *B. thuringiensis* subsp. kurstaki by EcoRI digestion and cloned these fragments into the vector Charon 4A. *E. coli* was infected with a recombinant bacteriophage, C4R6C, consisting of cloning vector Charon 4A and DNA from *B. thuringiensis*. These infected cells produced protein antigen which was the same size as the *B. thuringiensis* protoxin and protein extracts were toxic to neonate larvae of *Manduca sexta*. Hybridization of C4K6C DNA to *B. thuringiensis* plasmids indicated that the original Charon 4A clone contained the genes of chromosomal, no plasmid origin.

Wong et al (4) reported the nucleotide sequence of the promoter region and part of the coding region of the crystal protein gene from *B. thuringiensis* subsp. kurstaki HD-1-Dipel. A potential ribosome binding sit of 11 nucleotides was located three nucleotides upstream form the initiator ATG codon. The deduced sequence from the first 333 amino acids of the crystal protein was reported.

U.S. Pat. No. 4,448,885 describes plasmids capable of replicating in an *E. coli* bacterial host species which contains expressible heterologous DNA coding for a polypeptide of 130,000 daltons which has the immunological properties of the crystal protein of *B. thuringiensis*. Also disclosed is an *E. coli* bacterial strain transformed to express a polypeptide of 130,000 daltons which reportedly has immunological properties of the crystal protein of *B. thuringiensis*. A method of using said bacterial strains to produce an insecticidal effect is also disclosed.

Commercial insecticidal preparations containing spores and crystalline protein produced by *Bacillus thuringiensis* subsp. kurstaki are available as wettable powders and aqueous suspensions under such names as Dipel ® and Thuricide ®. These materials are used for the control of lepidoptera larvae such as Spruce budworm, cabbage looper, imported cabbage worm, gypsy moth, etc., which prey upon tobacco, cotton, soybeans, etc.

Major limitations to the use of commercial preparations of crystal protein toxin of *Bacillus thuringiensis* subsp. kurstaki include the need for repeated applications of the insecticidal preparations and limitation of the host range. Another drawback to the use of *B. thuringiensis* to produce insecticidal crystal protein is that the crystal protein is only produced during the sporulation stage of the *B. thuringiensis* life cycle. Such a growth phase limitation particularly in an industrial process, can result in inconvenience and excessive time requirements during manufacture. Pressures resulting from growth phase limitations or other factors may result in strains of *B. thuringiensis* losing their ability to produce the crystals; such acrystalliferous strains do not have insecticidal activity.

Although the isolation of DNA from *B. thuringiensis* subsp. kurstaki coding for the crystal protein toxin and the insertion of this DNA into expression vectors for the transformation of *E. coli* or *B. subtilis* is known, the prior art does not teach that such DNA can be inserted into a plant-colonizing microorganism in the first instance, nor the insertion of this DNA into the chromosome of a plant-colonizing microorganism to produce a plant-colonizing microorganism having insecticidal activity against insect pests. There is no teaching in the art that such plant-colonizing microorganisms can live and grow in the "plant environment" and give contact or systemic season-long insect control avoiding the need for repeated applications of the insecticidal crystal protein.

The delivery of insecticidal protein via a genetically engineered plant-colonizing microorganism which colonizes the "plant environment" and which expresses the insecticidal protein in the plant environment, i.e., on the leaf, stem, stalk, floral parts or root surface is unique and unexpected in view of the prior art which is directed to the production of the insecticidal crystal protein in culture, recovery of the protein from culture and the insecticidal application of preparations of mixtures of crystal protein and spores.

SUMMARY OF THE INVENTION

The invention relates to a plant-colonizing microorganism which has been genetically engineered to integrate into the chromosome of such microorganism, DNA derived from *B. thuringiensis* coding for the crystal protein toxin. The genetically engineered plant-colonizing microorganisms of the invention, and their progeny, proliferate in a non-detrimental relationship with the plant in the plant environment and are insecticidally active against a subspecies of lepidopterous larvae which are harmful to the plant. The invention further relates to insecticidal compositions containing such plant-colonizing microorganisms as the active insecticidal agent and to a method of using such genetically engineered plant colonizing microorganisms in a method of killing or inhibiting insect pests.

Integration of the *B.t.* gene, which expresses an insecticidal toxin, into the chromosome of the plant-colonizing microorganism provides the best means to prevent the transfer or loss of the introduced heterologous DNA. Although plasmids may be used to introduce cloned genes into a bacterium, they generally have inherent stability problems over many generations. Plasmids may also make the host bacterium less competitive because of their energy drain. Chromosomal insertion of the cloned trait decreases the likelihood that it will be mobilized conjugatively into other bacteria.

BRIEF DESCRIPTION OF THE DRAWINGS

Following is a brief description of the drawings which are not drawn to scale but are illustrative of materials which may be used in practicing the invention.

DETAILED DESCRIPTION OF THE INVENTION

The present invention is directed to a genetically engineered plant-colonizing microorganism which as integrated into its chromosome heterologous DNA which expresses a toxin having insecticidal activity against insects. A preferred embodiment of the invention is a protein having substantially the immunological properties of the crystal protein toxin of *Bacillus thuringiensis.* The invention further relates to the use of such plant-colonizing microorganisms in a method of inhibiting the growth and development of insect pests and to insecticidal compositions containing these plant-colonizing microorganisms as the active insecticidal agent.

Application Ser. No. 679,849, filed Dec. 10, 1984, entitled "Insertion of the *Bacillus thuringiensis* Crystal Protein Gene Into Plant-Colonizing Microorganisms And Their Use", the disclosure of which is herein incorporated by reference, describes the isolation of a 16 Kb fragment of plasmid DNA from *B. thuringiensis* coding for the insecticidal crystal protein toxin, the preparation of smaller fragments of DNA from the 16 Kb DNA fragment and the preparation of recombinant plasmids containing the various DNA fragments. The recombinant plasmids were transferred to plant-colonizing microorganisms where they expressed a protein which had the immunological properties of the crystal protein toxin of *B. thuringiensis* and which had insecticidal activity against insect larvae. The present invention is directed to the insertion of the DNA fragments described in application Ser. No. 679,849 into the chromosome of the plant-colonizing microorganism.

The term "plant-colonizing microorganism" is used herein to refer to as microorganism which is capable of colonizing the "plant environment" and which can express the insecticidal protein in the "plant environment". The plant colonizing microorganism is one which can exist in symbiotic or non-detrimental relationship with the plant in the plant environment. As used herein, the term "plant-colonizing microorganism" does not include spore forming organisms of the family Bacillaceae, for example, *Bacillus thuringiensis, Bacillus israelensis* and *Bacillus subtilis.*

The term "plant environment" refers to the surface of the plant, e.g., leaf, stem, buds, stalk, floral parts or root surface and to the "rhizosphere", i.e., the soil which surrounds and which is influenced by the roots of the plant.

Exemplary of the plant-colonizing microorganisms which may be engineered as taught herein are bacteria from the genera Pseudomonas, Agrobacterium, Rhizobium, Erwinia, Azotobacter, Azospirillum, Klebsiella, Alcaligenes and Flavobacterium. Rhizosphere colonizing bacteria from the genus Pseudomonas are preferred for use herein, especially the fluorescent pseudomonads, e.g., *Pseudomonas fluorescens* which is especially competitive in the plant rhizosphere and in colonizing the surface of the plant roots in large numbers. Another group of particularly suitable plant-colonizing microorganisms for use herein are those of the genus Agrobacterium; *A. radiobacter* has been found to be particularly suitable. Examples of suitable phylloplane colonizing bacteria are *P. putida, P. syringae,* and Erwinna species.

As used herein, the term "heterologous DNA" refers to DNA which is foreign to the plant-colonizing bacterium in which it resides and which codes for a protein having insecticidal activity against insect larvae and which is immunologically cross-reactive to the insecticidally active crystal protein toxin produced bu *B. thuringiensis.* The preferred "heterologous DNA" for use herein is DNA isolated from *B. thuringiensis* subsp. kurstaki. Both plasmid and chromosomal DNA, or a sub-fragmentation sequence thereof, may be used to genetically engineer the plant-colonizing microorganisms described herein. The synthetically produced equivalents may likewise be used and such use is contemplated herein.

The isolation of a plasmid DNA fragment (16 Kb) and the reduction of the isolated DNA fragment to smaller sub-units which express an insecticidally active protein is described in detail in application Ser. No. 679,849. Plasmid DNA from *B. thuringiensis* subsp. kurstaki HD-1 was used as the source of the crystal protein toxin gene. This strain was obtained from Dr. T. Yamamoto of the USDA—Bronwsville, Tex. There are a subspecies of publicly available *B. thuringiensis* strains which may likewise by used; e.g., *B. thuringiensis* subsp. kurstaki HD-1 (NRRL B-3792) and *B. thuringiensis subsp. kurstaki HD*-73 (NRRL B-4488). See also U.S. Pat. No. 4,277,564 and U.S. Pat. No. 4,448,885.

The initial plasmid DNA fragment isolated from the *B. thuringiensis donor strain was a* 16 Kb BamHI fragment which expressed protein that was immunologically reactive with antibody made to the 134,000 dalton crystal protein toxin of *B. thuringiensis*. The 16 Kb BamHI fragment was subcloned to produce an 8.1 Kb BamHI-PstI fragment. This fragment was further subcloned to produce a 4.6 Kb HpaI-PstI fragment. All of these DNA fragments coded for an insecticidally active protein toxin of about 134,000 daltons in size and which was immunologically reactive with antibody made tot he crystal protein toxin of *B. thuringiensis*. Various deletions of the *B.t.* crystal protein toxin gene were prepared by deleting DNA fragments from within the 8.1 Kb fragment. Deletions of mutations are contemplated for use herein to the extent that such deletions or mutations do not result in the loss of the insecticidal properties of the protein coded by the deletion or mutation fragments.

As described in detail herein, suicide plasmids carrying a transposon were used to integrate the *B.t.* DNA fragment into the chromosome of the plant-colonizing microorganism. However, as would be recognized by one skilled in this art, various other methods may be used to integrate the *B.t.* DNA into the chromosome.

As example, an in cis complementation system using Tn5 (5) can be used for the chromosomal integration of the *B.t.* DNA. Such a system uses Tn5 or Tn5 derivatives on a suicide plasmid or other plasmid systems based on incompatibility. The *B.t.* DNA along with the selectable marker gene (e.g., antibiotic resistance) is cloned into the interior of IS50L, such that the IS50L ends are not inactivated. Direct transposition of the IS50L containing the *B.t.* DNA and a selectable marker occurs into the chromosome of a plant-colonizing microorganism by selecting for the marker gene in IS50L. Transposase encoded by IS50R on the modified Tn5 is provided in cis for the transposition of IS50L. By screening the transconjugants for sensitivity to a Tn5-encoded gene (e.g., Kan$^R$, Ble$^R$ or Str$^R$), or a plasmid-encoded gene (e.g., Tet$^R$) or hybridization to specific DNA probes, one is able to distinguish between IS50L, composite Tn5 transposition events, and inverse transposition events.

The integration of the *B.t.* DNA into the chromosome of the plant-colonizing microorganism may also be mediated by homologous recombination using either a transposon, insertion sequence, phage, or chromosomal DNA from the target bacterium as the region of homology. Homologous recombination is mediated by DNA homology between the chromosome and a suicide plasmid or a plasmid in a system based on plasmid incompatibility in which a modified transposon (inactivated), insertion sequence (inactivated), phage (inactivated) or chromosomal DNA fragment contains the *B.t.* DNA cloned in its interior. The transposon, insertion sequence, phage or chromosomal segment in the recipient plant-colonizer is substituted by the modified transposon, insertion sequence, phage or chromosomal segment that now contains the *B.t.* DNA.

As used herein the term "suicide" plasmid refers to a plasmid vector which will mobilize into a cell but which will not be maintained. Suicide vectors are useful for transposon mutagenesis or site directed homologous recombination into any microbial strain into which they are mobilized but not stably maintained. Such plasmids are known in the art (6–11); Simon, et al (11) providing a good description of such useful plasmids.

The term "transposon" refers to a discrete genetic element that ensures its own maintenance by inserting into other autonomously maintained genetic elements in bacteria (12, 13). Transposons often encode phenotypes, such as antibiotic resistance. They are useful tools for genetic manipulations such as deletions, inversions and fusions (14). A transposon is a specific DNA segment with the ability to move as a unit in more or less random fashion from one genetic locus to another (15). Exemplary of specific transposons which may be used herein are those from the Tn3 family, Tn5, Tn7, Tn9, and Tn10. Especially preferred for use herein is the transposon Tn5 (16–18).

The plant-colonizing microorganisms of the invention are useful in a method of combatting Lepidoptera pests wherein an insecticidally effective amount of the plant-colonizing microorganism is applied to the plant environment or to the plant seed. The plant-colonizing microorganisms of the invention will have the same spectrum of insecticidal activity as the crystal protein toxin of *B. thuringiensis* subsp. kurstaki or berliner. Illustrative of the pest lepidoptera which are sensitive to *B.t.* crystal protein toxin and the crops such pests infest are: fall armyworm, European corn borer, Southwestern corn borer, corn earworm, common stalk borer and lesser corn stalk borer of corn; bollworms, pink bollworm, beet armyworm, and fall armyworm of cotton; velvet bean caterpillar, soybean looper, green cloverworm and beet armyworm of soybean; tobacco budworm and tobacco hornworm of tobacco; cabbage looper, imported cabbage worm, diamond back moth and beet armyworm of cole crops; rice stem borers of rice; Gypsy moth, Spruce budworm, cankerworm, tent caterpillars, and Douglas fir tussock moth of trees and shrubs.

The plant-colonizing microorganisms of the invention are useful for combatting insect pests other than lepidoptera by substituting an insecticidally active gene from a different subspecies of *B.t.* for the gene which expresses crystal protein toxin of the kurstaki subspecies. For example, Diptera may be controlled by recombinant microorganisms containing the protein toxin gene of *B. thuringiensis* subsp. Israelensis, European Patent Application No. 8501017.1 Publication No. 0153166. Colonization of aquatic plants by these microorganisms may control mosquitoes and other Diptera. Coleoptera, e.g., Colorado potato beetle, cotton boll weevil and soybean weevil, may be controlled by a recombinant microorganism containing the protein toxin gene of B.t. subsp. tenebrionis, European Patent Application No. 8411535.1, Publication No. 0149162.

The methods and composition of this invention are effective against any insects susceptible to *B. thuringiensis* insecticidal proteins. Examples of such insects either in the form of adults or larvae are described in Table 1, pages 60–70, of Australian Patent Application 33473/84, the disclosure of which is incorporated herein by reference.

The insecticidal plant-colonizing microorganisms of the invention may be applied directly to the plant environment, e.g., to the surface of the leaves, buds, roots or floral parts or to the plant seed. When used as a seed coating, the plant-colonizing microorganisms of the invention are applied to the plant seed prior to planting. Generally, small amounts of the insecticidally active microorganism will be required to treat such seeds.

The determination of an insecticidally effective amount of plant-colonizing microorganisms useful in the method of the invention required for a particular plant is within the skill of the art and will depend on such factors as the plant species, method of planting, and the soil type, (e.g., pH, organic matter content, moisture content).

Theoretically, a single plant-colonizing microorganism of the invention (containing the toxin gene) is sufficient to control insect pests because it can grow into a colony of clones of sufficient number to express insecticidal amounts of toxin. However, in practice due to varying environmental factors which may affect the survival and propogation of the microorganism a sufficient number of bacteria should be provided in the plant environment (roots or foliage) to assure survival. For example, application of $10^3$ to $10^{10}$ bacteria per seed was sufficient to insure colonization on the surface of the roots by the microorganism. Typically 0.2 to 200 nanograms of toxin per insect will provide adequate control. It is preferred to dose the plant environment with enough bacteria to maintain a population which expresses 50 to 250 nanograms of toxin. For example, $10^5$ to $10^8$ bacteria per square centimeters of plant surface is adequate to control insect infestations. At least 0.5 nanograms, preferably 1 to 100 nanograms of insecticidally active protein per insect is sufficient to control insect damage to plants.

Compositions containing the insecticidally active plant associated microorganism of the invention are prepared by formulating the biologically active microorganism with adjuvants, diluents, carriers, etc. to provide compositions in the form of finely-divided particulate solids, granules, pellets, wettable powders, dusts, aqueous suspensions or dispersions, and emulsions. Illustrative of suitable carrier vehicles are: solvents e.g., water or organic solvents and finely divided solids, e.g., kaolin, chalk, calcium carbonate, talc, silicates and gypsum.

It is contemplated herein to use the insecticidal microorganisms in the methods and compositions of the invention in encapsulated form; e.g., the plant-colonizing microorganism can be encapsulated within shell walls of polymer, gelatin, lipid and the like or other formulation aids as for example emulsifiers, dispersants, surfactants, wetting agents, anti-foam agents and anti-freeze agents, may be incorporated into the insecticidal compositions, especially if such compositions will be stored for any period of time prior to use.

In addition to the insecticidally active plant-colonizing microorganism the compositions of the invention may additionally contain other known biologically active agents, as for example, a herbicide, fungicide, or other insecticide. Also, two or more insecticidally active plant-colonizing microorganism may be combined.

The application of insecticidal compositions containing the genetically engineered plant-colonizing microorganisms of the invention as the active agent can be carried out by conventional techniques utilizing, for example, spreaders, power dusters, boom and hand sprayers, spry dusters and granular applicators.

The compositions of the invention are applied at an insecticidally effective amount which will vary depending on such factors as, for example, the specific lepidopteran larvae to be controlled, the specific plant to be treated and method of applying the insecticidally active compositions.

The following examples illustrate specific embodiments of the invention described herein. As would be apparent to skilled artisans, various changes and modifications are possible and are contemplated within the scope of the invention described.

Isolation of a 16 Kb DNA fragment coding for the crystal protein toxin of B. thuringiensis preparation of smaller fragments of insecticidally active DNA from the 16 Kb fragment and insertion of such fragments into plasmids was carried out as described in Example 1.

EXAMPLE 1 a. Starting Microorganism

B. thuringiensis subsp. kurstaki HD-1 utilized herein as the source of plasmid DNA for the recombinant plasmids was obtained from Dr. Takashi Yamamoto of the United States Department of Agriculture (USDA). B. thuringiensis strains were maintained as sporulated stock cultures according to standard procedures. Cultures were routinely monitored for crystal production by phase contrast microscopy.

b. Preparation of Synthetic Oligonucleotide Probes

The amino acid sequence of the crystal protein toxin gene isolated from Bacillus thuringiensis subsp. kurstaki HD-1 was partially determined according to the method of Hunkapiller et al (19). These sequences were verified using the DNA sequence of the $NH_2$-terminal portion of the crystal protein gene disclosed by Wong et al (4). Synthetic oligonucleotide sequences based on an amino acid sequence determined from the crystal protein polypeptide were prepared according to the procedure of Beaucage et al (20). The oligonucleotide probes prepared are as shown in Table I.

TABLE I

| SYNTHETIC OLIGONUCLEOTIDE PROBES | | |
|---|---|---|
| Size | Probe Sequence | Area of B.t. Protein |
| 14-mer | TGG GGA CCG GAT TC | 219-223 amino acid region* |
| 14-mer | GAA AGA ATA GAA AC | 27-31 amino acid region* |
| 21-mer | CCT GAA GTA GAA-GTA TTA GGT | 19-25 amino acid region* |

*numbered from $NH_2$— terminal end c. Preparation and Isolation of Plasmid DNA From B. thuringiensis

Plasmid DNA from B. thuringiensis subsp. kurstaki HD-1 was purified from 1 liter of culture according to the procedure of Kronstad et al (21). All plasmid preparations were banded at least once in CsCl/ethidium bromide gradients. Plasmids 30 megadaltons and larger in size were preferentially isolated.

Digestion with restriction enzymes EcoRI, PstI, HindIII, BamHI and SmaI, was carried out according to conditions recommended by the supplier (Boehringer Mannheim). Escherichia coli strain JM 101 (22) and strain SR-200 (23) were used as the recipients for the transformation step. Competent cells were prepared according to standard procedures (24). Colonies transformed with plasmid pUC8, were plated on L-agar with 100 μg/ml of ampicillin and 40 μl of 4% 5-bromo-4-chloro-3-indolyl-β-D-galactopyranoside (x-gal).

Cloning vectors used herein are known in the art and are generally available. Choice of a particular vector is within the skill of the art and is largely a matter of individual preference. Plasmid vectors which may be mentioned as being suitable for use herein are identified in Table II.

TABLE II

| Plasmid Vector | Brief Description | Reference |
|---|---|---|
| pBR328 | — | Bolivar, F., (1978) Gene 4:121 |
| pUC7 | — | Vieira, J. and Messing, J. (1982) Gene 19:259 |
| pUC8 | Multi-site pBR322 ATCC 37017 like vector | Vieira, J. and Messing, J. (1982) Gene 19:259 |
| pMON5008 | Derivative of pKT230 | USSN 592,158 filed 3/21/84 |
| pUC18 | | Strain Kit "M13 mp/pUC" Cat. #824055 available from Bethesda Research Laboratories, Life Technologies, Inc. Gaithersburg, MD 20877 |
| pGS9 | | Selvaraj, and Iyer, V. N. (1983) J. Bacteriol 156: 1292-1300 |
| pSUP101 | pACYC 184 + mob fragment of RP4 | Simon et al (1983) Biotechnology 1:784-791. |
| pSUP1011 | pACYC 184 + mob fragment of RP4 + Tn5 | Simon et al (1983) Biotechnology |
| pSUP1021 | pACYC 184 + mob fragment of RP4 + Tn5 | Simon et al (1985) Methods in Enzymology Plant Molecular Biology. Academic Press | d. Preparation of Nitrocellulose Filters and Hybridization

Plasmid DNA fragments separated on an agarose gel were transferred to nitrocellulose according to the procedure of Southern (25). Prehybridization was done by incubating the nitrocellulose paper with the bound transferred DNA in pre-hybridization fluid, 10× Denhardt's (0.2% BSA, 0.2% Ficoll, 0.2% polyvinylpyrrolidone) and 6× SSC (0.9M NaCl, 0.09M sodium citrate) for 2-4 hours at 37° C. Hybridization was done by incubating the nitrocellulose paper for 8-10 hours with 10-11 ml of the pre-hybridization fluid and the labelled probe. After several washes with 6× SSC at increasing temperatures (30-45° C.) the paper was exposed to X-ray film.

e. Cloning of the B.t. toxin gene in E. coli

BamHI-restricted pBR328 (100 ng), treated with alkaline phosphate (Boehringer Mannheim) was mixed and ligated with 500 nj of B. thuringiensis plasmid DNA restricted with BamHI. CaCl$_2$ prepared competent E. coli SR200 were transformed and selected by ampicillin resistance and screened for tetracycline sensitivity. Analysis by mini-plasmid prep procedures (26) identified two clones which had a 16 Kb insert. Southern hybridization analysis with radiolabelled probes from Table I demonstrated that the DNA fragment which contained the sequence hybridizing to the synthetic probe had been cloned. The two plasmids, designated pMAP1 and pMAP2, differed only in the orientation of the DNA fragment within the vector. These plasmid constructs produced material cross-reactive to B.t. crystal protein toxin antibody when analyzed according to Western blot procedures (27). A restriction map of the inserted B.t. fragment was prepared and four EcoRI (E) sites and three Hind III (H) sites were located between the BamHI (B) sites. This is schematically illustrated as:

```
B   E    E E E                    B
         H H    H
```

E. coli SR200 containing pMAP2 has been deposited with the ATCC and has been designated ATCC #39800.

f. Sub-cloning of B.t. Toxin

AN 8.1 Kb BamHI-PstI fragment was isolated after BamHI-PstI digestion of pMAP2 by electroelution from a preparative agarose gel onto DEAE paper used according to the directions of the manufacturer Schleicher & Schuell (28). Plasmid pUC8 was used to sub-clone the BamHI-PstI fragment of pMAP2 carrying the B.t. gene. Ligation of pUC8 digested with BamHI and PstI with the purified 8.1 Kb BamHI-PstI fragment was followed by transformation of competent E. coli JM101. Transformants were selected on the basis of ampicillin resistance and a lack of β-galactosidase activity. A clone was isolated and was confirmed to contain the desired plasmid. This construct was designated pMAP3. E. coli JM101 containing pMAP3 has been deposited with ATCC and has been designated ATCC #39801.

Figure 1:
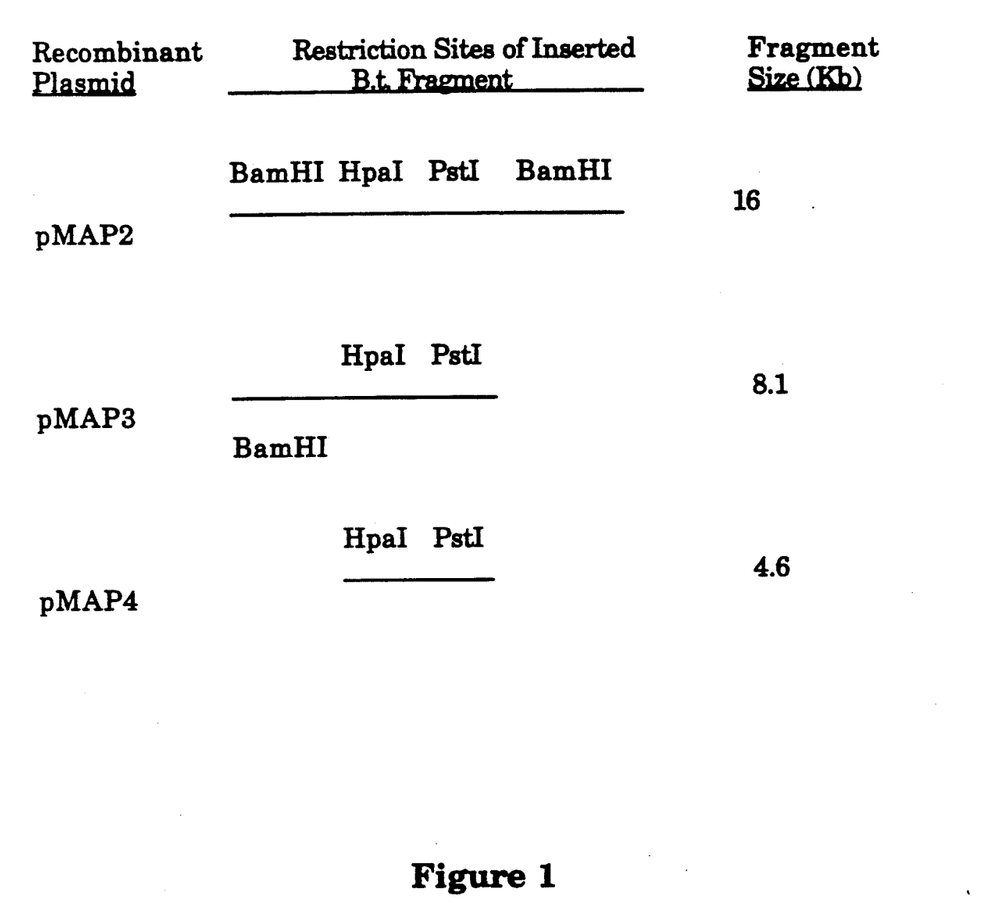
FIG. 1 is a partial restriction endonuclease cleavage map of the inserted *B.t.* fragment of pMAP2, pMAP3 and pMAP4.

Reduction of the B,. thuringiensis DNA insert of pMAP3 from 8.1 to 4.6 Kb was done by deleting a SmaI-HpaI fragment. Plasmid pMAP3 DNA, purified by CsCl gradient centrifugation was digested with SmaI and HpaI restriction enzymes and religated. The resulting DNA fragment was utilized to transform competent E. coli JM101 cells. Ampicillin resistant transformants were screened by agarose electrophoresis of mini-plasmid preparations. A clone was identified which contained a plasmid with the expected DNA restriction enzyme digestion pattern. This construct was labelled pMAP4. The above-described sub-cloning of the 16 Kb insert of pMAP2 containing the B. thuringiensis toxin gene to an 8.1 Kb insert (pMAP3) and a 4.6 Kb insert (pMAP4) is illustrated in FIG. 1.

g. Insertion of DNA Isolated From B.t. Into cloning Vector pMON5008

Plasmid pMON5008 constructed by B. C. Hemming and D. J. Drahos of Monsanto Company was used as a cloning vector to transform competent cells of E. coli with a 4.6 Kb fragment of plasmid DNA isolated from pMAP3. Plasmid pMON5008 is a derivative of plasmid pKT230; construction of pMON5008 is described in U.S. Ser. No. 592,158 filed Mar. 21, 1984, which is commonly assigned to Monsanto Company and the disclosure of which is herein incorporated by reference.

In order to get proper insertion of the 4.6 Kb fragment isolated from pMAP3 into pMON5008 adjustments to the ends of the 4.6 Kb fragment were required. A PstI linker (CCTGCAGG) was added to the 4.6 Kb HpaI-PstI fragment as described below.

Plasmid pMAP3 (10 μg) was digested with HpaI; complete digestion was confirmed by agarose gel analysis. The digest was extracted with mixture of phenol/chloroform (1:1), followed by chloroform extraction and finally by ethanol extraction. The resulting precipitate was washed with TE buffer, (0.01M TRIS/0.001M EDTA, pH 8.0 and thereafter resuspended in same. Two μg of PstI linker (CCTGCAGG) obtained from New England Biolabs was combined with 2 units of T4 DNA kinase in a total volume of 10 μl of kinase/ligase buffer. The mixture was incubated at 37° C. for 1 hour. Thereafter, 2 μg of the kinase/linker mixture was added to 2 μg of HpaI digested pMAP3 and 2 μl of T4 DNA ligase (2 units) and the resulting mixture was incubated for 18 hours at 22° C. after which 1 μl of 0.5M EDTA (pH 8.0) was added and the mixture was extracted as described above. The resulting precipitate was washed with TE buffer and resuspended in 90 μl of fresh TE buffer. The precipitate was digested with PsTI and the digest was mixed with 6.0 μl of 5M NaCl and run through a Sepharose CL-4B column. The fractions were collected and were screened by agarose gel electrophoresis. Fractions containing high molecular weight DNA were combined, precipitated, and the resulting precipitate was washed with TE buffer and thereafter resuspended in fresh TE buffer.

The DNA which was collected from the column was mixed with PstI digested plasmid vector pUC7 which had been treated with alkaline phosphatase and column-purified. The PstI-PstI fragment was ligated into the PstI site of pUC7 and used to transform competent *E. coli* JM101. Inserting the *B.t.* gene into the unique PstI site of pUC7 positioned the gene between two BamHI sites.

Ampicillin resistant β-gal negative transformants were selected and were analyzed for the correct plasmid construct by mini-plasmid preparations and restriction endonuclease digestion. A plasmid with a 4.6 Kb fragment flanked by both PstI and BamHI sites was isolated and designated pMAP8.

Plasmid pMON5008 DNA was isolated, digested with BamHI or BglII, treated with alkaline phosphatase and purified on a Sepharose CL-4B column. A mixture of 1 ug of this vector DNA and 2 ug of pMAP8 digested with BamHI was ligated and used to transform competent *E. coli* cells. Transformants were selected by their kanamycin resistance and screened by restriction endonuclease digestion of the plasmid DNA isolated by mini-plasmid preparation. Constructs with *B.t.* DNA inserted at both the BamHI and BglII sites of pMON5008 in both orientations were obtained and identified as pMAP12, pMAP13, pMAP14 and pMAP15.

h. Preparation of Deletion Derivatives Of the *B.t.* Toxin Gene

Figure 2:
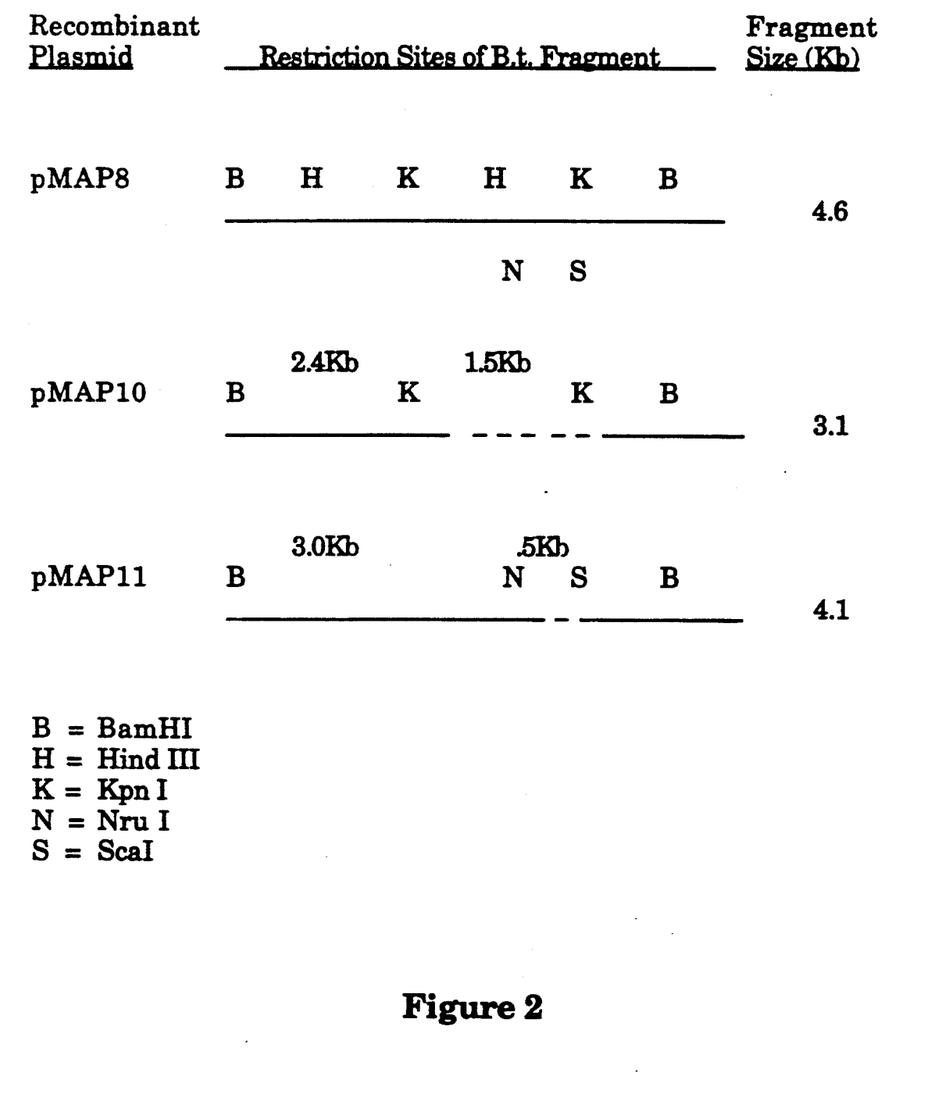
FIG. 2 is a partial restriction endonuclease cleavage map of the inserted *B.t.* fragment of pMAP8, pMAP10 and pMAP11.

Deletion derivatives of the *B.t.* crystal protein toxin gene were prepared by deleting DNA fragments of pMAP8 within the coding region of the 134,000 dalton toxin. Plasmid pMAP8 (1–1.5 ug in 20 uL of TE buffer was cut with the appropriate enzyme(s), extracted with a phenol/chloroform mixture (1:1), diluted to 40 uL with TE buffer, re-ligated and used to transform CaCl$_2$-competent JM101 cells. Plasmids with deletions were identified by screening mini-prep plasmid preparations on agarose gels after electrophoresis. Two deletion derivatives, designated pMAP10 and pMAP11, were constructed by deleting a 1.4 Kb KpnI fragment (pMAP10) and a 0.5 Kb NruI-ScaI fragment (pMAP11) from pMAP8. *E. coli* with either of these constructs produced material toxic to Manduca sexta. The restriction map of the deletion fragments is shown in FIG. 2.

The 2.4 Kb BamHI-KpnI fragment of pMAP10 was subcloned in pUC18. pMAP10 and pUC18 were digested with BamHI and KpnI, mixed, ligated and used to transform *E. coli* JM101. A clone was isolated which contained a plasmid with a single 2.4 Kb BamHI-KpnI fragment. This plasmid was designated pMAP18. *E. coli* containing this plasmid were toxic to Manduca sexta.

EXAMPLE 2

Cloning of DNA Into Tn5 On The Plasmid Vector pGS9

One hundred (100) μg of pMAP8 was digested to completion with BamHI restriction endonuclease and the resulting 4.6 Kb (BamHI *B.t.* DNA) and 2.5 Kb (pUC7 vector) fragments were separated on a preparative 0.7% agarose gel. The 4.6 Kb *B.t* fragment (target DNA) was purified by electroelution, ion exchange chromatography through an Elutid-D column (Scleicher and Schuell), and ethanol precipitation. Ten (10) μg of the 4.6 Kb *B.t.* fragment was treated with calf intestinal alkaline phosphatase (25U) prior to cloning into the transposon Tn5 of the suicide vector pGS9.

Figure 3:
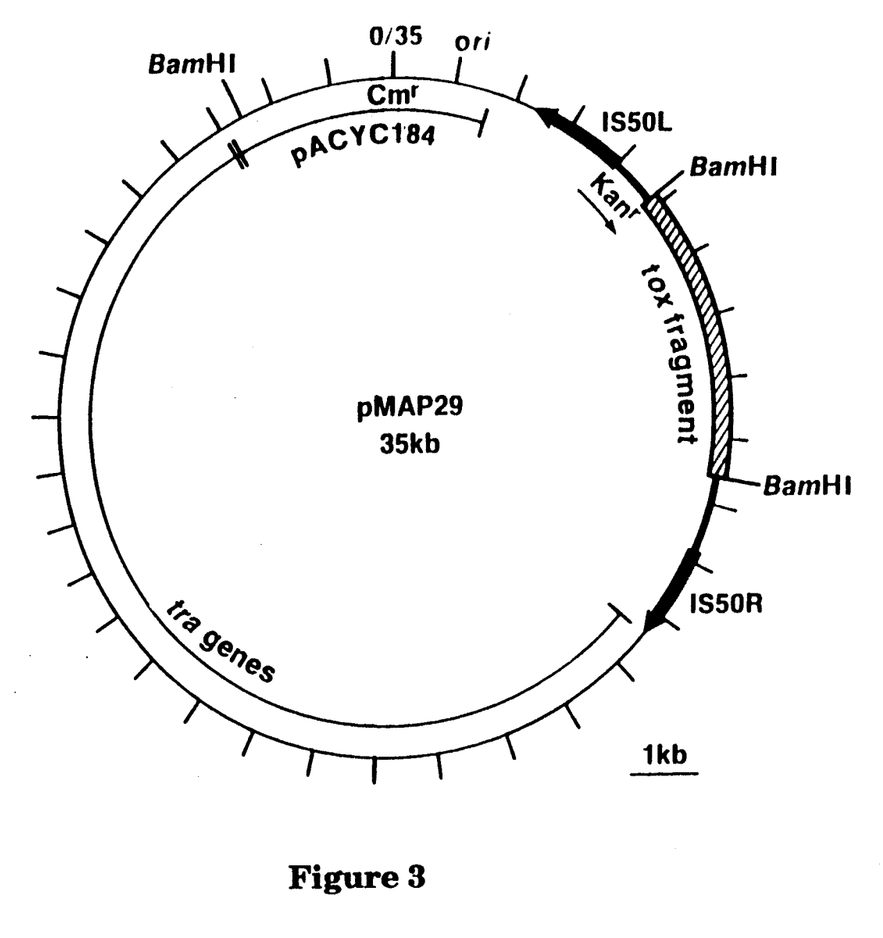
FIG. 3 is a partial restriction endonuclease cleavage map of pMAP29.

Ten (10) μg of vector pGS9 DNA was digested to completion with BAMHI. Target and vector DNA were phenol extracted, ethanol precipitated, and resuspended in TE buffer prior to mixing them in different pmolar end ratios (target:vector ratios of 1:1, 3:1, and 9:1). Target and vector DNA were mixed in a total of 25 μl reannealing buffer (10 mm Tris, pH 7.5, 100 mm NaCl) for approximately five hours. Twenty-five (25) μl 2×ligation buffer plus 1 μl T4 DNA ligase were then added. Ligation was done overnight at 14° C. The resulting plasmid, i.e., pGS9 containing the 4.6 Kb *B.t.* DNA fragment inserted into Tn5 at the BamHI site with the Kan$^R$ gene and the *B.t.* gene in the same orientation was identified as pMAP29 and has the restriction map shown in FIG. 3. Plasmid pMAP30 was prepared having the BamHI-*B.t.* DNA fragment in the opposite orientation within Tn5 (Kan$^R$ gene and the *B.t.* gene in opposite orientation). Neither Kan$^R$ nor transposase was affected by the insertion of the 4.6 Kb *B.t.* DNA fragments into Tn5 of pGS9.

The *B.t.* DNA fragments prepared and isolated as described in Examples 1 and 2 were used to genetically engineer plant-colonizing microorganisms as described below. Before the *B.t.* DNA was inserted into the chromosome of a plant-colonizing microorganism it was first necessary to provide a method of identifying those plant-colonizing microorganisms which were engineered. Example 3 describes the isolation of plant-colonizing microorganisms having the ability to grow in the presence of the antibiotics rifampicin and nalidixic acid.

EXAMPLE 3

Isolation of Plant-Colonizing Microorganisms Having Antibiotic Resistance

Spontaneous rifampicin resistant strains were obtained by plating 1×10$^9$ colony forming units (CFU) of the plant-colonizing microorganism on an L-agar plate with 100 μg/ml rifampicin to obtain rifampicin resistant (Rif$^R$) mutants. Similarly, spontaneous nalidixic acid resistant strains were obtained by plating $1 \times 10^9$ CFU of the spontaneous Rif$^R$ strain on an L agar plate with 100 µg/ml nalidixic acid. Alternatively, nalidixic acid resistant (Nal$^R$) mutants were obtained by exposing $1 \times 10^{10}$ CFU of the Rif$^R$ mutant to UV light in 5 ml of L-broth in an open petri plate on a gently rotating shaker. Exposure times ranged from 1 to 8 minutes. Exposed colonies were plated on L-agar with 100 µg/ml of nalidixic acid. Isolated single colonies were grown under non-selective conditions at 30° C. in L-broth and plated on media with and without nalidixic acid. Bacterial strains were routinely grown on 2% L-agar (29) or on 2% Vogel-Bonner Minimal medium (30).

Following the above procedure, several strains of plant-colonizing bacteria were rendered resistant to rifampicin and nalidixic acid; these strains were identified as follows:

| Plant-Colonizing Bacterium | Designation |
| --- | --- |
| Pseudomonas fluorescens | 112-12 |
| Pseudomonas fluorescens | 121-5 |
| Pseudomonas fluorescens | 3732-3-7 |
| Pseudomonas fluorescens | 421-24 |
| Agrobacterium radiobacter | 212-4 |
| Agrobacterium radiobacter | 212-7 |

EXAMPLE 4

Transformation of E. coli with pMAP29

E. coli HB101 was used in the transformation step. This strain, which is a good host for large-scale growth and purification of plasmids (31), has the genotype: F$^-$, hsdS20 (r$^-$$_B$m$^-$$_B$), rec A13, ara -14, pro-A2, lac Y1, gal K2, rpsL20 (Sm$^R$), xyl-5, mtl-1, supE44, A$^-$. CaCl$_2$ competent E. Coli HB101 cells were transformed with the ligation mixture (BamHI-digested pGS9 plus the BamHI B.t. gene fragment from pMAP8. The procedure (32) was modified in the respect that 50 mM CaCl$_2$ was used without 10 mM Tris-HCl. The cells were made competent 40 minutes on ice. DNA was then added and the cells were kept an additional 30 min. on ice prior to heat pulse treatment at 42° C. Transformed E. coli HB101 was used as the donor in the conjugal matings that followed.

EXAMPLE 5

Conjugal Matings a. Filter matings

Donor strains (E. coli HB101/pMAP29 or HB101/pMAP30) and recipient strains of the plant-colonizing microorganisms were grown overnight in 5 ml of L-broth supplemented with the appropriate antibiotics. After centrifugation, the bacteria were suspended in 0.9% NaCl. Aliquots were transferred to fresh L-broth without antibiotics and were grown to mid-log phase (40 Klett units; 20 Klett units for A. radiobacter 212-4 and 212-7). Cells, 1 ml each of donor and recipient, were mixed and mated on a 0.45 micron Millipore filter (2.5 cm diameter) placed on 1% L-agar overnight at 30° C. (33). For controls, 1 ml of donor and 1 ml of recipient bacteria were incubated separately. After mating, the filters were mixed thoroughly in 1 ml 0.9% NaCl. Ten-fold serial dilutions were made in 0.9 ml of 0.9% NaCl. Tenth (0.1) ml aliquots were plated on LB agar containing 100 µg/ml of rifamficin to counter-select against the E. coli donors and 50 µg/ml of kanamycin to select for Tn5 or Tn5-B.t. transposition events.

Liquid Matings

Donor and recipient bacteria were grown as described for the filter matings. On ml each of mid-log phase donor and recipient cells were mixed in a test tube and then grown together overnight with vigorous shaking at 30° C. After mating, the bacterial suspension was diluted in 0.9% NaCl and 0.1 ml aliquots were plated on the appropriate selective medium. Counter-selections were carried out using the chromosomal marker Rif$^R$. All transconjugants were purified by single colony isolation on second plates containing the appropriate antibiotics prior to analysis.

Pseudomonas fluorescens 3732-3-7A (Tn5-B.t.) was deposited with ATCC and has been designated ATCC #39912. Pseudomonas fluorescens 112-12A (Tn5-B.t.) was deposited with ATCC and has been designated ATCC #39913.

Data showing the frequency of the strains of plant-colonizing bacteria acquiring Tn5 and Tn5-B.t. a result of the conjugal matings are shown in Table III.

TABLE III

| Donor | Recipient | Selected Marker | Counter-selection | Number of Transconjugants Per Donor | Number of Transconjugants Per Recipient |
| --- | --- | --- | --- | --- | --- |
| E. coli HB101/pGS9 | 112-12 | Kan (Tn5) | LB agar + rif | $2.5 \times 10^{-6}$ | $1.2 \times 10^{-7}$ |
| E. coli HB101/pGS9 | 121-5 | " | " | $3.5 \times 10^{-9}$ | $1.7 \times 10^{-11}$ |
| E. coli HB101/pGS9 | 212-4 | " | " | $4.5 \times 10^{-6}$ | $4.9 \times 10^{-7}$ |
| E. coli HB101/pGS9 | 212-7 | " | " | $2.4 \times 10^{-8}$ | $2.9 \times 10^{-9}$ |
| E. coli HB101/pGS9 | $^a$3732-3-7 | " | " | $<5.0 \times 10^{-8}$ | $<3.5 \times 10^{-11}$ |
| E. coli HB101/pGS9 | 421-24 | " | " | $1.4 \times 10^{-7}$ | $1.5 \times 10^{-8}$ |
| E. coli HB101/pMAP29 | 112-12 | Kan (Tn5-B.t.) | LB agar + rif | $6.5 \times 10^{-7}$ | $1.9 \times 10^{-8}$ |
| E. coli HB101/pMAP29 | $^b$121-5 | " | " | $<2.8 \times 10^{-9}$ | $<2.1 \times 10^{-11}$ |
| E. coli HB101/pMAP29 | 212-4 | " | " | $5.0 \times 10^{-6}$ | $4.0 \times 10^{-7}$ |
| E. coli HB101/pMAP29 | 212-7 | " | " | $1.0 \times 10^{-8}$ | $7.3 \times 10^{-10}$ |
| E. coli HB101/pMAP29 | $^c$3732-3-7 | " | " | $<1.4 \times 10^{-7}$ | $<2.5 \times 10^{-11}$ |

TABLE III-continued

| Donor | Recipient | Selected Marker | Counter-selection | Number of Transconjugants Per Donor | Number of Transconjugants Per Recipient |
|---|---|---|---|---|---|
| E. coli HB101/pMAP29 | 421-24 | " | " | $1.1 \times 10^{-7}$ | $2.7 \times 10^{-9}$ |

<sup>a</sup>Upon repeating the experiment using the original E. coli WA803 donor containing pGS9, putative Tn5-containing transconjugants were obtained at a very low frequency ($5 \times 10^{-11}$/recipient or $7 \times 10^{-9}$/donor).
<sup>b</sup>Liquid mating with vigorous shaking overnight yielded a single transconjugant ($1.5 \times 10^{-11}$/recipient).
<sup>c</sup>Liquid mating with vigorous shaking overnight yielded two transconjugant ($6.1 \times 10^{-11}$/recipient).

EXAMPLE 6

Confirmation of Presence of Tn5—B.t. DNA Fragment

The presence of the Tn5-B.t. DNA fragment within the chromosome of the plant-colonizing microorganism was confirmed by Southern hybridization analysis. In all cases, only a single copy of Tn5-B.t. was integrated into the chromosome of the plant-colonizing transconjugants. The Tn5-*B.t.* insertions were in different chromosomal locations (34).

Whole cell DNA (chromosomal plus plasmid) was prepared according to procedure 25 of Silhavy et al (35). The procedure was scaled down ten-fold so that 10 ml of an overnight culture was used. Two slight modifications were incorporated for preparing the DNA from root colonizers. After the first ethanol precipitation, the DNA was dissolved in 2 ml Tris buffer. After the second ethanol precipitation, the DNA was dissolved in 0.5 ml Tris buffer.

Whole cell DNA was isolated from randomly chosen Tn5-*B.t.* putative transconjugants, one Tn5 putative transconjugant, and the $Rif^R$ $Nal^R$ parent from each of the six root-colonizing strains. Cellular DNA (5 $\mu$g) was digested to completion with BamHI, separated on 0.8% agarose gels, and blotted onto membrane filters (Biodyne A filters). Southern blot transfer was performed according to Silhavy et al (35)(procedure 44). The procedure was modified by using a sponge as the wick.

Plasmid pMAP29 was nick translated with $\alpha$-$^{32}$P-dATP (Silhavy et al, procedure 48). Unincorporated $\alpha$-$^{32}$P-dATP was separated from incorporated $\alpha$-$^{32}$P-dATP on a 10 ml Sephadex G-50 column. The probe consisted of approximately $1.3 \times 10^6$ Cerenkov cpm. DNA-DNA hybridization was performed according to Silhavy et al procedure 46.

The results of the DNA-DNA hybridization analysis indicated that the Tn5-*B.t.* DNA fragment was integrated at a single chromosomal site in all of the plant-colonizers examined. Each transconjugant of a given strain had Tn5-*B.t.* located at a different position.

The plant-colonizing microorganisms of the invention were tested for insecticidal activity according to the following examples. In the examples which follow, protein extracts of the plant-colonizing microorganism or unlysed cell preparations were used. Protein extracts were prepared as shown in Example 7.

EXAMPLE 7

Preparation of Protein Extract

Fifty milliliters of L-broth containing 100 $\mu$g/ml ampicillin was inoculated with the microorganism (control or engineered plant-colonizing microorganism) and the inoculum was maintained overnight at 30° C. on a shaker. The inoculum was centrifuged for ten minutes in an SS-34 rotor at 10K. The pellet was resuspended in 5 ml of Ellis buffer (pH 10.5) with 10 mM DTT. The suspension was quickly frozen on dry ice and thereafter thawed in a water bath maintained at about 30° C. Thereafter, 1 ml of glass beads (Thomas Scientific #5663 R50) was added to the suspension and the mixture vortexed for about 15 seconds. This procedure was repeated 8 times. The glass beads were removed by centrifuging through glass wool. The lysed cell sample was collected and added to an equal volume of Ellis buffer (pH 6.5). The extract was then used in the insect assay(s). The amount of insecticidal protein expressed in several of the plant-colonizing microorganisms of the invention were estimated based on ELISA (36) immunological analysis of soluble protein and Western Blot analysis of total protein.

Example 8 describes the insect assay used herein to test the genetically-engineered plant-colonizing microorganisms of the invention for insecticidal activity.

EXAMPLE 8—DIET ASSAY

A standard artificial diet medium was dispensed into 3.0×4.0 cm flat bottom wells to a volume of ca. 5 ml. The agar based diet hardened within a short period of time and was thereafter treated with the test (or control) material. 100 ul of test (or control) material was applied with an automatic pipettor to the surface of each of 10 wells of diet. An alcohol flamed glass spreader was used to spread the material to insure an even coating. The treated trays were allowed to dry under a vertical flow hood before placing one neonate larvae on the diet surface of each of 10 wells (10 larvae/treatment). The trays were then sealed and incubated at 28° C. for 4 days prior to evaluating the percent mortality induced by the treatment. Control treatments were included in each assay to check the effects of the diet and the non-engineered microorganism.

EXAMPLE 9

*P. fluorescens* 112-12 containing the 4.6 Kb *B.t* BamHI DNA fragment inserted in its chromosome was tested against neonate *Manduca sexta* (tobacco hornworm) larvae using the diet assay of Example 8. The strains were grown overnight in 5 ml of Luria Broth (LB) at 30° C. to stationary phase without antibiotics. Tenth ml aliquots were used directly in the assay. *E. coli* HB101 containing pMAP29 and *P. fluorescens* without *B.t.* DNA were used as controls. All of the 112-12(Tn5-*B.t.*) transconjugants gave 100% mortality. The results are summarized in Table IV.

TABLE IV

| Treatment | % Corrected Mortality |
|---|---|
| Ps. 112-12 | 0 |
| Ps. 112-12(Tn5) | 10 |
| Ps. 112-12-A (Tn5-B.t.) | 100 |
| *E.coli* HB101/pMAP29 | 100 |
| Untreated | 0 |
| Ps. 3732-3-7 | 0 |
| Ps. 3732-3-7 (Tn5) | 10 |

TABLE IV-continued

| Treatment | % Corrected Mortality |
| --- | --- |
| Ps. 3732-3-7A (Tn5-B.t.) | 100 |
| E.coli HB101/pMAP29 | 100 |
| Untreated | 0 |

EXAMPLE 10

*P. fluorescens* 3732-3-7A and *P. fluorescens* 112-12A were tested against tobacco hornworm larvae using the diet assay of Example 8. The strains were grown as described in Example 9. The cultures were centrifuged and the cell pellets resuspended in 5 ml. of saline (0.9% NaCl). Ten and 100× dilutions were made in saline. The LB supernatants were filter-sterilized. For each sample, 100 μl of the undiluted, 10× dilution, 100× dilution, and undiluted supernatant broth were assayed. Both orientations of the *B.t.* gene within Tn5 were tested for the two strains. The results which are summarized in Table V illustrate that the orientation of the *B.t.* gene within Tn5 affects the amount of *B.t.* protein produced. Based on Western blotting analysis and *M. sexta* toxicity, more *B.t.* toxin was synthesized when the Kan$^R$ promoter of Tn5 is in the same orientation as the native *B.t.* promoter.

TABLE V

| | Undiluted % CM | Broth Filtrate % CM | $10^{-1}$ Dilution % CM | $10^{-2}$ Dilution % CM |
| --- | --- | --- | --- | --- |
| Treatment | | | | |
| 112-12 | 0 | 0 | — | — |
| 112-12(Tn5) | 0 | 0 | — | — |
| 112-12A(Tn5-B.t.) | | | | |
| #1* | 100 | 0 | 100 | 32 |
| #2* | 100 | 10 | 100 | 21 |
| #3** | 100 | 0 | 66 | 0 |
| #4** | 100 | 0 | 66 | 21 |
| 3732-3-7 | 0 | 0 | — | — |
| 3732-3-7/Tn5 | 0 | 0 | — | — |
| *3732-3-7A(Tn5-B.t.) | 100 | 0 | 100 | 100 |
| Strain | | | | |
| E. coli HB101 (pMAP29) | 100 | 0 | — | — |
| 0.9% NaCl | 0 | — | — | — |
| Luria Broth | — | 0 | — | — |
| Untreated | 0 | 0 | — | — |

*Kan$^R$ and B.t. promoters in same orientation.
**Kan$^R$ and B.t. promoters in opposite orientation (opposed).
% CM = % corrected mortality Titration experiments were carried out to determine the relative LD$_{50}$ values of *P. fluorescens* 3732-3-7 (Tn5-*B.t.*) and *P. fluorescens* 112-12 (Tn5-*B.t.*) The LD$_{50}$ values for *P. fluorescens* 112-12(Tn5-*B.t.*) and *P. fluorescens* 3732-3-7-(Tn5-*B.t.*) varied slightly from mid-log to stationary growth phase. Strain 3732-3-7-(Tn5-*B.t.*) was more toxic at mid-log phase (LD$_{50}$=2.7×10$^6$ CFU/ml) than at stationary phase (LD$_{50}$=4.9×10$^6$ CFU/ml). In 112-12(Tn5-*B.t.*), the stationary phase sample was more toxic (LD$_{50}$=3.3×10$^6$ CFU/ml) than at mid-log phase (LD$_{50}$1.2×10$^7$ CFU/ml).

EXAMPLE 11

3732-3-7A(Tn5-*B.t.*) and 112-12A (Tn5-*B.t.*) grown as described in Example 9 were tested for activity against larvae of the black cutworm (agrotis ipsilon) in the diet assay of Example 8. Aliquots (100 μl) of the culture were used directly in the assay. The results which are summarized in Table VI indicate that exposure of black cutworm larvae to 112-12(Tn5-*B.t.*) and 3732-3-7(Tn5-*B.t.*) resulted in mortality and weight loss in comparison to the parenteral controls and the untreated larvae.

TABLE VI

| Treatment | % Corrected CM | Av. Larvae Weight (mg) |
| --- | --- | --- |
| 112-12(Tn5-B.t.) | 38 | 211.6 |
| 112-12 | 0 | 274.0 |
| 3732-3-7(Tn5-B.t.) | 16 | 223.6 |
| 3732-3-7 | 0 | 238.8 |
| Untreated | 0 | 290.8 |

EXAMPLE 13

3732-3-7A(Tn5-*B.t.*) and 112-12A(Tn5-*B.t.*) were tested against beet armyworm (*Spodoptera exiqua*), soybean looper (*Pseudoplusia includens*), cabbage looper (*Trichoplusia ni*) and corn earworm (*Heliothis sea*) in the standard diet assay described in Example 8. The strains were grown according to the procedure of Example 9. The results observed when 100 μl aliquots of the culture was applied to the insect larvae are summarized in Table VII.

TABLE VII

| Treatment | SE % CM | TN % CM | PI % CM | HZ % CM |
| --- | --- | --- | --- | --- |
| 3732-3-7A | *0 | 100 | 87 | *10 |
| 112-12A | **0 | 100 | 0 | **0 |
| Untreated | 0 | 0 | 0 | 0 |

* = Growth Suppression of Larvae Observed
** = Severe Growth Suppression of Larvae Observed
SE = Beet armyworm
TN = Cabbage looper
PI = Soybean looper
HZ = Corn earworm
% CM = % Corrected Mortality The construction of transposase-minus Tn5-*B.t.* derivatives prepared by homologous recombination and by IS50L transposition are described in Examples 14 and 15, respectively.

EXAMPLE 14

(a) Plasmid Construction

Plasmid pSUP1021 (11) was used as the parental vector in the Mob+host *E. coli* S17-1. This plasmid is suicidal, encodes non-transposable Tc$^R$ and Cm$^R$ and contains a wild-type Tn5 element (Kan$^R$Ble$^R$ Str$^R$) located within the mob region. The plasmid is mobilized from E. coli S17-1 by transfer proteins provided in trans by an integrated RP4-2-Tc:: Mu-KM::Tn7 helper plasmid (15). The transposase gene of Tn5 is contained within one of the two inverted terminal insertion sequences denoted IS50R (37).

In constructing a transposase deletion derivative, (ΔTn5) the Hind III site in IS50R (position 1196) was first converted to a BgI II site by cutting this site with Hind III, filling in the 5′ overhangs, and ligating BgI II linker fragments to the resulting blunt-ended DNA. An internal deletion within Tn5 from the Bgl II site in IS50L (position 1516) to the newly created Bgl II site in IS50R (position 1196) was made by a Bgl II digestion and subsequent ligation. This plasmid is referred to as pMAP101. The structure of pMAP101 was verified by restriction enzyme analysis. The deletion removed all of the interior of Tn5 (Kan$^R$, Ble$^R$, Str$^R$) as well as 320 bp of the transposase gene in IS50R, but left the NPT II promoter in IS50L intact.

Insertion sequence IS50L encodes an inactive transposase gene due to the presence of an ochre termination codon (38). A second mutation was created in the transposase gene of IS50L in both the pSUP1021 parental plasmid and the pMAP101 ΔTn5 derivative. A (+)4 frameshift mutation was created at the XhoI site of IS50L (position 486) in both pSUP1021 and pMAP101 by cutting this site with XhoI, filling in the 5′ overhangs, and ligating the resulting blunt-ended DNA (pMAP108, and pMAP109 respectively). A PvuI site was created as a result of the fill-in and ligation. Verification of the proper fill-in and ligation was done by restriction enzyme analysis. Frameshift mutants of IS50L are referred to as Tn5-1 elements.

The 4.6 kb Bam HI B.t. delta-endotoxin gene fragment (preparation described in Example 15) was cloned into the unique BglII site of pMAP109 in the same orientation as the NPT II promoter, giving plasmid pMAP111. A 6.2 kb BglII Kan$^R$-B.t. delta-endotoxin gene fragment (preparation described in Example 15) was also cloned into the unique BglII site of pMAP109 in the same orientation as the NPTII promoter, giving plasmid pMAP110.

The Tn5-B.t. transposase deletion derivatives from pMAP111 (ΔTn5-1 B.t.) have a 320 bp deletion of the transposase gene in IS50R and a frameshift mutation in the transposase gene of IS50L.

b. Construction of Tn5-1-Containing Recipients of Ps112-12 and Ps3732-3-7

Filter matings between the E. coli S17-1 (pMAP108) donor and the recipient strains Ps112-12 and Ps3732-3-7 were performed to obtain chromosomal insertions of Tn5-1 (Kan$^R$, low-level Str$^R$, (+)4 frameshift mutation in IS50L). Kanamycin resistant transconjugants of Ps112-12 and Ps3732-3-7 were obtained at a frequency of approximately 10$^{-7}$/recipient. The Kan$^R$ transconjugants were also Str$^R$, but Tet$^S$, verifying the presence of Tn5-1 and absence of pMAP108 in the chromosome. The chromosomal Tn5-1 element provided homology for the recombination event with the transposase deletion elements ΔTn5-1Kan$^R$-B.t. on plasmid pMAP110 and ΔTn5-1 B.t. on plasmid pMAP111.

c. Tn5-1/pMAP110 and Tn5-1/pMAP111 Cointegrate Intermediate Formation in Ps112-12 and Ps3732-3-7

Plasmid pMAP110 containing ΔTn5-1Kan$^R$-B.t. and plasmid pMAP111 containing ΔTn5-1 B.t. from the E. coli S17-1 donor integrated into the chromosome of four 112-12 (Tn5-1) recipients and two 3732-3-7 (Tn5-1) recipients by homologous recombination provided by Tn5-1 sequences. The frequency of cointegrate intermediate formation was 10$^{-6}$ $^{TetR}$ transconjugants/recipient using standard filter matings. No Tet$^r$ transconjugants were obtained when either Ps112-12 or Ps3732-3-7 was used as a recipient because no Tn5 homology was present. Eight Tet$^R$ transconjugants (cointegrate intermediates) from each of the matings were purified on a nonselective medium (LB agar). Single colonies were then patched onto LB agar+kan, LB agar+str, LB agar+tet, LB agar+rif, LB agar+nal, and VB minimal medium to make certain that they had the expected markers. All but one of the cointegrate intermediates had the expected markers (Kan$^R$, Str$^R$, Tet$^R$, Rif$^R$, Nal$^R$, and VB+). The single exception (Str$^S$) was discarded.

d. Resolution of Cointegrate Intermediates: Screening for ΔTn5-1Kan$^R$-B.t. and ΔTn5-1B.t. Recombinants of Ps112-12 and Ps3732-3-7

Resolution of the pMAP 110 and pMAP111 cointegrate intermediates occur by homologous recombination during growth in a non-selective medium (e.g. LB) giving $Tet^s$ recombinants. Screening using replica plating was carried out to obtain two classes of Tn5-*B.t.* transposase deletion elements in Ps112-12 and Ps3732-3-7; 1) ΔTn5-1 $Kan^R$-*B.t* where $Kan^R$ was a marker juxtaposed to the *B.t.* delta-endotoxin gene and 2) ΔTn5-1 *B.t.* containing the *B.t.* delta-endotoxin gene but where no phenotyic marker was present. Both classes of recombinants contain the 320 bp transposase deletion in IS50R as well as the frameshift mutation in the transposase gene of IS50L.

Cointegrate intermediates of Ps112-12 and Ps3732-3-7 were thus inoculated into LB agar from cultures patched on LB agar and grown overnight to stationary phase at 30° C. (approximately $3\times10^9$ cfu/ml). The appropriate dilution for each culture was plated onto LB agar+rif plates to obtain approximately 150 cfu/-plate. Replica-plating was then done onto: (1) LB agar+tet and LB agar+kan when screening for ΔTn5-1 *B.t.* recombinants ($Kan^s$, $Str^s$, $Tet^s$) and 2) LB agar+-tet and LB agar+str when screening for ΔTn5-1$Kan^4$-*B.t.* recombinants ($Kan^R$, $Str^s$, $Tet^s$). Putative recombinants were obtained using 112-12 (Tn5-1) and Ps3732-3-7 (Tn5-1) recipients with Tn5-1 in at least two different chromosomal locations. A total of 34 putative recombinants of Δtn5-1$Kan^R$-*B.t.* and ΔTh5-1 *B.t.* were obtained at a frequency between $10^{-3}$–$10^{-4}$. All putative recombinants obtained by replica plating were single colony purified on LB agar plates. Single colonies were then patched onto 1) LB agar+tet, 2) LB agar+ kan, 3) LB agar+str, 4) LB agar+rif, 5) LB agar+nal, and 6) VB minimal medium. All of the putative recombinants except one had the proper markers ($Kan^R$, $Tet^S$, $Str^S$, $Rif^R$, $Nal^R$, VB+ for ΔTn5-1$Kan^R$-*B.t.* recombinants; $Kan^S$, $Tet^S$, $Str^S$, $Rif^R$, $Nal^R$, VB+ for ΔTn5-1*B.t.* recombinants).

Western blot analysis showed that all but three of the 34 putative ΔTn5-1$Kan^R$-*B.t.* and ΔTn5-1 *B.t.* recombinants of Ps112-12 and Ps3732-3-7 produced the 134 KDal *B.t.* delta-endotoxin.

*Meduca sexta* bioassays verified the western blotting results. All but three of the 34 putative ΔTn5-1Kan$^R$-*B.t.* and ΔTn5-1 *B.t* recombinants gave 100% mortality against *M. sexta* larvae.

The XhoI site in IS50L where the (+)4 frameshift mutation was made in ΔTn5-1 Kan$^R$-*B.t.* and ΔTn5-1 *B.t.* is *fairly close to the left end of Tn5* (position 486). In order to recombine the IS50L (+)4 frameshift mutation from ΔTn5-1 *B.t.* or ΔTn5-1 *B.t.* into the chromosome of a recipient carrying a wild-type Tn5, the recombination step has to occur to the left of the XhoI site. Since more homology exists to the right of the XhoI site in the IS50L element of pMAP101 (1.0 kb vs. 0.5 kb, respectively), recombination is more likely to occur to the right of the XhoI site. Such a recombination event would still retain the non-mutated XhoI site in IS50L. To avoid this possibility, the identical (+)4 frameshift mutation at the XhoI site in IS50L of the pSUP1021 parental plasmid was made (Tn5-1 element) (pMAP108). When the Tn5-1 element is used as a portable region of homology in the chromosome of Ps112-12 or Ps3732-3-7, the identical frameshift mutation in IS50L is present on the incoming suicidal plasmid, pMAP110 containing ΔTn5-1Kan$^R$-*B.t.* or pMAP111 containing ΔTn5-1 *B.t.* All of the ΔTn5-1Kan$^R$-*B.t.* or ΔTn5-1 *B.t.* recombinants of Ps112-12 or Ps3732-3-7 would then contain this frameshift mutation in IS50L, provided that the two Tn5 elements in the cointegrate intermediate were in the same orientation. This is the case when the Tn5 sequences align themselves properly prior to plasmid integration (right end with right end and lift end with left end). If the two Tn5 elements in the cointegrate intermediate were in inverted orientation, less than a 50% chance existed that the recombination event would include the IS50L (+)4 frameshift mutation. This is the case when the Tn5 sequences align themselves in opposite orientation prior to plasmid integration (right end with left end or left end with right end). The 320 bp transposase deletion in IS50R is present in the ΔTn5-1Kan$^R$-*B.t.* or ΔTn5-1 *B.t.* recombinants, regardless of the orientation in the cointegrate intermediate.

e. Southern Hybridizations: Analysis of Putative ΔTn5-1Kan$^R$-*B.t.* and ΔTn5-1 *B.t.* Recombinants of Ps112-12 and Ps3732-3-7

Hybridization results showed that the ΔTn5-1Kan$^R$-*B.t.* and ΔTn5-1*B.t.* recombinants of Ps112-12 and Ps3732-3-7 had the proper structure. Each ΔTn5-1Kan$^R$*B.t.* and ΔTn5-1*B.t.* recombinant pair of Ps112-12 and Ps3732-3-7 had the same junction fragments using either HindIII-PvuI or HindIII-XhoI double digests. Results of the HindIII-PvuI hybridization showed that the ΔTn5-1Kan$^R$*B.t.* and ΔTn5-1*B.t.* recombinants had the same IS50L junction fragment as the Tn5-1 parental element. The IS50R junction fragment of the recombinants was approximately 1.5 kb larger than the IS50R junction fragment of the Tn5-1 parental element because the HindIII site was absent in the deleted IS50R element of the recombinants. Results of the HindIII-XhoI hybridization showed that the recombinant pairs had the same IS50L and IS50R junction fragments as the ΔTn5-1Kan$^R$*B.t.* and ΔTn5-1*B.t.* elements. This indicates that ΔTn5-1Kan$^R$-*B.t.* and ΔTn5-*B.t.* are at the same chromosomal site and in the same orientation as the Tn5-1 parental element. All of the expected internal ΔTn5-1Kan$^R$*B.t.* or ΔTn5-1*B.t.* fragments were accounted for by the HindIII-PvuI and HindIII-XhoI double digests. The 0.75 kb HindIII-PvuI fragment of IS50L was present in the ΔTn5-1Kan$^R$*B.t.* and ΔTn5-1*B.t.* recombinants, showing that the +4 frameshift mutation in the transposase gene of IS50L was present. This fragment was present in the Tn5$_{-1}$ parental element. The 0.75 kb HindIII-XhoI fragment in the ΔTn5-1Kan$^R$*B.t.* and ΔTn5-1*B.t.* recombinants was absent, showing that the transpose deletion in IS50R was present. This fragment was present within the Tn5-1 parental element.

Hybridization results showed that all of the expected fragments of the cointegrate intermediates were present. Both possibilities of cointegrate intermediates with the two Tn5 elements in the same orientation were observed. It was expected that the two Tn5 elements in the cointegrate intermediate would be in the same orientation. Only these cointegrate intermediate structures would yield recombinant elements of ΔTn5-1Kan$^R$*B.t.* or ΔTn5-1*B.t.* that have the same orientation as the parental Tn5-1 element.

f. Homologous recombination mediated by Tn5 was used to integrate two classes of Tn5-*B.t.* transposase deletion elements into the chromosome of the *P. fluorescens* root colonizers, Ps112-12 and Ps3732-3-7. A Tn5-*B.t.* transposase deletion element was substituted for a Tn5 element previously present in the chromosome. The first class (ΔTn5-1Kan$^R$-*B.t.*) encodes Kan$^R$ along with the *B.t.* delta-endotoxin while the second class (ΔTn5-1 *B.t.*) only encodes the *B.t.* delta-endotoxin without a selectable marker. In both classes, 320 bp of the 3' end of the transposase gene of IS50R was deleted (BglII-Hind III in IS50R). Both classes also contain a (+)4 frameshift mutation at position 486 (former XhoI site) in addition to the natural single base pair transversion from G-C to T-A at position 1443 in the transposase gene of IS50L. Both classes of Tn5-*B.t.* transposase deletion elements are incapable of independently transposing to a new site.

The recombinants were designated as follows:
Ps112-12 (ΔTn5-1Kan$^R$-*B.t.*)=Ps112-12B
Ps112-12 (ΔTn5-1 *B.t.*)=Ps112-12C
Ps3732-3-7 (ΔTn5-1Kan$^R$-*B.t.*)=Ps3732-3-7B
Ps3732-3-7 (ΔTn5-1 *B.t.*)=Ps3732-3-7C Ps112-12C was deposited with ATCC and has been designated ATCC No. 53279. The two sets of recombinants contain ΔTn5-1Kan$^R$-*B.t.* and ΔTn5-1 *B.t.* at the same chromosomal site and in the same orientation as the parental Tn5-1 element. All four recombinants produced B.t. delta-endotoxin as assessed by western blotting and *M. sexta* bioassays. ELISA assays have shown that the *B.t.* delta-endotoxin comprises approximately 0.5-1% of the total soluble cellular protein in Ps112-12 and Ps3732-3-7.

EXAMPLE 15

Use of IS50L Transposition to Insert Transposase Negative Fragments of DNA Containing the *B.t. kurstaki* Delta-Endotoxin Gene into the Chromosome of Root Colonizers (a) Derivatives of Ps112-12 and Ps3732-3-7 containing a chromosomal IS50L (Kan$^R$-*B.t.* element were obtained by a direct transposition method. The direct transposition method used IS50L from Tn5 as a translocatable supplied insertion sequence that required transposase supplied in cis from IS50R. A frameshift mutation was made in the transposase gene of the IS50L (Kan$^R$-*B.t.* element at the former XhoI site (position 486). Two separate mutations are thus present in the transposase gene of the IS50L (Kan$^R$-B.t.) element (+4 frameshift mutation at position 486 and the natural single base pair transversion from G-C to T-A at position 1443).

(b) Plasmid Construction

Plasmid pSUP1011 was used as the parental vector in the Mob+ host E. coli SI7-1 (Simon et al., 1983). This plasmid cannot replicate in non-enteric Gram-negative bacteria, encodes non-transposable Cm, and contains a wild-type Tn5 element. Transposon Tn5 encodes resistance to kanamycin (neomycin phosphotransferase II, NPTII), bleomycin (ble, unknown resistance mechanism), and streptomycin (streptomycin phosphotransferase). The three antibiotic resistance genes comprise an operon that utilizes a common promoter located between the PvuII and BglII sites of IS50L (NPTII promoter). Plasmid pSUP1011 is mobilized from E. coli SI7-1 by transfer proteins provided in trans by an integrated RP4-2-Tet::Mu-Kan::Tn7 helper plasmid (Simon et al., 1983).

A 6.2 kb BglII fragment containing the Kan$^R$ and Bk$^R$ resistance genes of Tn5 juxtaposed to the B.t. delta-endotoxin gene was inserted into an IS50L element (IS50L (Kan$^R$-B.t.) contained on a pSUP1011 derivative in several steps. A 4.6 kb BamHI fragment containing the *B.t.* delta-endotoxin was first inserted into the unique GamHI site of Tn4 in plasmid pSUP1011 in the same orientation as the $Kan^R$ gene, making pMAP37. The large 7.4 kb BglII internal fragment form the Tn5-*B.t.* construct was then inserted into the unique BglII site of the pBR322-derived multi-copy cloning vector, pMON7068, making pMAP512. A BglII site was made at the 3' BamHI site of the *B.t.* delta-endotoxin gene in pMAP512 by performing a partial BamHI digestion, 5' fill-in reaction, and blunt end ligation with BglII linkers. This 6.2 kb BglII fragment containing the $Kan^R$, $Ble^R$ and *B.t.* delta-endotoxin genes was then inserted into the unique BglII site of pMON7068, making pMAP514.

A 700 bp deletion in the interior of Tn5 of pSUP1011 was made by a Bal31 digestion from the SmaI site, inactivating the $Kan^R$ gene. The 6.2 BglII fragment containing the $Kan^R$, $Ble^R$, and *B.t. l delta-endotoxin genes from pMAP*514 was inserted into the BglII site of IS50L (IS50L ($Kan^R$-*B.t.*)) of pMAP33 downstream from the NPTII promoter (pMAP515)). The IS50L inside end recognition sequences were kept intact (19 bp) and transposase was supplied in cis by an intact IS50R. The Kan gene in the interior of Tn5 of pSUP1011 was deleted (pMAP33) in order to avoid duplicate copies with the $Kan^R$ gene present in IS50L ($Kan^R$-*B.t.*).

A frameshift mutation in the transposase gene of the IS50L ($Kan^R$-*B.t.*) element was also constructed at the XhoI site of IS50L (position 486) by cutting this site with XhoI, filling in the 5' overhangs, and ligating the resulting blunt-ended DNA. This sequence of reactions introduces a four bp insertion (+4 frameshift) and also creates a new PvuI site. Verification of the proper fill-in and ligation was done by restriction enzyme analysis; the XhoI site in IS50L was lost and a new PvuI site was created (pMAP517). Plasmid pMAP517 was used for delivery of IS50L ($Kan^R$-*B.t.*) into the chromosome of 112-12 and Ps3732-3-7 by selecting for $Kan^R$ transconjugants.

(c) Screening for the Transposition of IS50L($Kan^R$-*B.t.*) into the Chromosome of 112-12 and Ps3732-3-7

Filter matings were performed using *E. coli* SI7-1 (pMAP517) as donor and strains 112-12 and 3732-3-7 as recipients. The mobilization of pMAP517 was checked by using *E. coli* K802 (40) a recipient which stably maintains the plasmid. Kanamycin resistant transconjugants of 112-12 and Ps3732-3-7 were obtained at a frequency of approximately $10^{-7}$ recipient. Mobilization of pMAP517 into *E. coli* K802 occurred at a frequency of approximately $10^{-2}$ recipient. Assuming the same frequency of mobilization into 112-12 and Ps3732-3-7, the combined frequency for the three possible types of transposition products from pMAP517 was approximately $10^{-5}$ recipient.

In order to distinguish IS50L ($Kan^R$-*B.t.*) transposition events from composite or inverse transposition events, a series of colony hybridizations was carried out using two different DNA fragments as probes. The first probe was the 1.2 kb BamHI-BglII fragment from the internal BamHI site of Tn5 to the BglII site of IS50R. A positive hybridization signal indicated that a composite transposition event occurred. A negative hybridization signal indicated that either an IS50L ($Kan^R$-*B.t.*) or inverse transposition event occurred. The second probe not containing any Tn5 sequences was the 1.5 kb EcoRI-HindIII fragment from the pMAP517 vector plasmid. A positive hybridization signal indicated that an inverse transposition event occurred. A negative hybridization signal indicated that either an independent IS50L ($Kan^R$-*b.t.*) or composite transposition even occurred. Approximately 90–95% of the Kan% transconjugants contained composite transposition products and 5–10% contained either inverse or independent IS50L ($Kan^R$-*B.t.*) transposition products. Transconjugants that did not hybridize to either probe contained IS50L ($Kan^R$-*B.t.*).

One colony each of the Ps112-12 and Ps3732-3-7 transconjugants that contained IS50L ($Kan^R$-*B.t.*) after colony hybridizations was confirmed by Southern hybridization restriction enzyme mapping. Double digests (HindIII-PvuI and HindIII-XhoI) of chromosomal DNA from the transconjugants and the plasmid vector pMAP517 were performed. The fragments were separated by agarose gel electrophoresis, transferred to Biodyne A membranes, and probed with nick translated pMAP517. Hybridization results showed that the putative 112-12 and Ps3732-3-7 transconjugants in fact contained a single chromosomal copy of IS50L ($Kan^R$-*B.t.*). The presence of the 0.75 kb PvuI-HindIII fragment confirmed the frameshift mutation in the transposase gene of IS50L ($Kan^R$-*B.t.*). The remainder of the internal PvuI-HindIII fragments (3.7 kb and 1.0 kb) or XhoI-HindIII fragments (2.1 kb, 1.6 kb, and 1.0 kb) verified the structure of IS50L ($Kan^R$-*B.t.* ). The absence of the 4.0 kb HindIII fragment and 0.75 kb HindIII-XhoI fragment eliminated the possibility of a composite transposition product. Similarly, the absence of the 1.8 kb PvuI-HindIII fragment and 5.8 kb and 0.75 kb HindIII-XhoI fragments eliminated the possibility of an inverse transposition product.

Western Blot Analysis

Western blot analysis showed that both Ps112-12/IS50L ($Kan^R$-*B.t.*) and Ps3732-3-7/IS50L ($Kan^R$-*B.t.*) produced a 134 kdal *B.t.* delta-endotoxin

Manduca sexta Bioassays

*Manduca sexta* bioassays verified the western blotting results. Both PS112-12/IS50L (Kan$^R$-*B.t.*) and Ps3732-3-7/IS50L(Kan$^R$-*B.t.*) gave 100% mortality against *M. sexta* larvae. The Ps112-12 and Ps3732-3-7 parental controls were not toxic.

Direct transposition using an in cis complementation system was used to insert an IS50L(Kan$^R$-*B.t.*) element into the chromosome of the *P. fluorescens* root colonizers, Ps112-12 and Ps3732-3-7. A 6.2 kb BglII fragment encloding Kan$^R$, Ble$^R$, and the *B.t.* delta-endotoxin was inserted into the BglIII site of IS50L downstream from the NPTII promoter. By utilizing a derivative of the suicidal vector pSUP1011 pMAP517) and providing transposase in cis from an intact is50R element, independent IS50L(Kan$^R$-*B.t.*) transposition events into the chromosome of Ps112-12 and Ps3732-3-7 were obtained.

These strains containing IS50L(Kan$^R$-*B.t.*) were designated as follows:

Ps112-12/IS50L(Kan$^R$-*B.t.*)=Ps112-12D
Ps3732-3-7/IS50L(Kan$^R$-*B.t.*)=Ps3732-3-7D

Ps112-12D was deposited with ATCC and has been designated ATCC No. 53280. Both strains produce *B.t.* delta-endotoxing as assessed by western blotting and *M. sexta* bioassays. ELISA assays have shown that *B.t.* delta-endotoxin comprises approximately 1% of the total soluble cellular protein in Ps112-12D and Ps3732-3-7D.

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein.

REFERENCES

1. Schnepf, H. E., and Whitely, H. R. (1981). Cloning and Expression of the *Bacillus thuringiensis* Crystal Protein in *Escherichia coli.* Proc. Natl. Acad. Sci. USA, 78:2893–2897.
2. Klier, A., Fargette, F., Ribier, J. and Rapoport, G. (1982). Cloning and Expression of the Crystal Protein Genes From *Bacillus thuringiensis* strain berliner 1715. *EMBO J.* 1:791–799.
3. Held, G. A., Bulla, L. A., Ferrari, E., Aronson, A. I. and Minnich, S. A. (1982). Cloning and Localization of the Lepidopterans Protoxin Gene of *Bacillus thuringiensis* sub-sp. kurstaki. Microbiology, 79: 6065–6069. Held, G. A., et al, Proc. Natl. Acad Sci. USA, 79:6065–6069.
4. Wong, H. C., Schnepf, H. E., and Whiteley, H. E. (1983). Transcriptional and Translational Start Sites For The *Bacillus thuringiensis* Cyrstal Protein Gene. J. Biol. Chem. 258:1960–1967.
5. Berg, D. E., Johnsrud, L., McDivitt, L., Ramabhadian, R. and Hirschel, B. J. (1982). Inverted Repeats of Tn5 and Transposable /Elements, Proc. Natl. Acad. Sci., USA 79: 2632–2635. See also, Mazodier, P., Cossart, P., Giraud, E. and Gasser, F. (1985). Completion of the Nucleotide Sequence of the Central Region of the Tn5 Confirms The Presence of Three Resistance Genes. Nucleic Acids Research. 13: 195–205.
6. Selvarj. G. and Iyer, V. N. (1983). Suicide Plasmid Vehicles For Insertion Mutagenesis in Rhizobium meliloti and Related Bacteria. J. of Bacteriology. 156: 1292–1300.
7. Alton, N. K., and D. Vapnek. (1979). Nucleotide Sequence Analysis of the Chloramphenicol Resistance Transposon Tn9. Nature (London) 282:846–869.
8. Beringer, J. E. et al. (1978). Transfer of the Drug Resistance Transposon Tn5 to Rhizobium. Nature (London) 276: 633–634.
9. Casadesus, J. E. et al. (1980). Transposition of Tn1 to the *Rhizobium meliloti* Genome. *Mol. Gen. Genet.* 180:405–410.
10. Van Vliet, F., Van Montagu, M. Shell, J. (1978). Transfer of RP4:: Mu Plasmids to *Agrobacterium tumefaciens.* Plasmid 1: 446–445.
11. Simon, R., O'Connell, M., Labes, M., and Puhler, Al. (1985). Plasmid vectors For the Genetic Analysis and Manipulation of Rhizobia and Other Gram-Negative Bacteria. In H. Weissbach and A. Weissbach (eds.), Method in Enzymology, Plant Molecular Biology.
12. Kleckner, N. (1981). Transposable Elements in Prokaryotes Annu. Rev. Genet. 15: 341–404.
13. Starlinger, P. (1980). IS Elements and Transposons. Plasmid 3: 241–259.
14. Kleckner, N., J. Roth, and D. Botstein. (1977). Genetic Engineering in vivo Using Translocatable Drug Resistance Elements, J. Mol. Biol. 116:125–159.
15. Simon, R., et al. (1983). A Broad Host Range Mobilization System For In Vivo Genetic Engineering: Transposon Mutagenesis In Gram Negative Bacteria.BIO/TECHNOLOGY Nov. 1983.
16. Mazodier, P., Giraud, E., and Gasser, F. (1983). Genetic analysis of the streptomycin resistance encoded by Tn5. Mol. Gen. Genet. 192:155–162.
17. Putnoky, P., Kiss, G. B., Ott, I., and Kondorose, A. (1983). Tn5 carries a streptomycin resistant determinant downstream from the kanamycin resistance gene. Mol. Gen. Genet. 191:288–294.
18. Reznikoff, W. S. (1982). Tn5 transposition and its regulation. Cell. 31:307–308.
19. Hunkapiller, M. W., Hewick, R. M., Dreyer, W. J., and Hood, L. E. (1983) Methods Enzymol. 91:399–413.
20. Beaucage, S. L. and Caruthers, M. H. (1982). Tetrahedron Lett. 22:1859–1862; see also Addams, S. P. et al. (1983) JACS. 105:661–663.
21. Kronstad, J. W., Schnepf, H. E., and Whitely, H. R. (1983). Diversity of locations for *Bacillus thuringiensis* crystal protein genes. J. Bacteriol. 154:419–428.
22. Messing, J., Crea, R. and Seeburg, P. H. (1981). Nucleic Acids Research. 9:309–321.
23. *Escherica coli* SR200 was obtained from Dr. S. G. Rogers of Monsanto Co., St. Louis. Mo. 61637.
24. Dagert, M. and Ehrlich, S. D. (1979) Gene 6:23–28.
25. Southern, E. M. (1975). J. Mol. Biol. 98:503–517.
26. Maniatis, T., Fritsch, E. G., and Sambrook, J. (1982). *Molecular Cloning A Laboratory Manual,* Cold Spring Harbor, N.Y., p. 396.
27. Towbin, H., Staehelin, T. and Gordon (1979). PNAS, USA. 76:4350–4354.
28. Schleicher & Schuell, Inc. Keene, N. H., 03431, USA, "Binding and Recovery of DNA and RNA Using SIS NA-45 DEAE Membrane", *Sequences-Application Update,* No. 364.
29. Lennox, E. S. (1955). Transduction of listed genetic characters of the host bacteriophage Pl. Virology. 1:190–206.

30. Vogel, H. and Bonner, D. M. (1956). Acetylornithase of *Escherichia coli:* Partial purification of some properties. J. Biol. Chem. 218:97–106.
31. Bolivar, F., et al. (1977). Construction and characterization of new cloning vehicles. II. A new cloning system. Gene. 2: 95–113.
32. *Molecular Cloning* (ibid) p. 250.
33. Chatterjee, A. K. and Starr, M. P. 1973. Gene transmission among strains of *Erwinia amylovora.* J. Bacteriol. 116:1100–1106.
34. Berg, D. E., Egner, C., Hirschel, B. J., Howard, J., Johnsrud, L., Jorgensen, R. A. and Tlsty, D. (1981). Insertion, excision, and inversion of Tn5. Cold Spring Harbor Symp. Quant. Biol. 45:115–123.
35. Silhavy, T. J., Berman, M. L., and Enquist, L. W. (1984). *Experiments with Gene Fusions.* Cold Spring Harbor Laboratory, Cold Spring Harbor, N.Y.
36. *The Enzyme Linked Immunosorbent Assay, A Guide With Abstracts of Microplate Applications.* A. Voller, D. Bidwell and A. Bartlett (1979) Dynatech Laboratories, Inc., Alexandria, Va.
37. Johnson, R. C. and Reznikoff, W. S. (1984) Role of the IS50R Proteins in the Promotion and Control of Tn5 Transposition, J. Mol. Biol. 177:645–661.
38. Rothstein, S. J. and Reznikoff, W. S. (1981). The Functional Difference in the Inverted Repeats of Tn5 Are Caused by a Single Base Pair non-homology. Cell. 23:191–199.
39. Nag, D. K., Das Gupta, U., Addt, G., and Berg. D. E. (1985). IS50-Mediated Inverse Transposition: Specificity and Precesion. Gene 34:17–26.
40. Strain *E. coli* K802 was obtained from Dr. P. D. Shaw, Dept. of Plant Pathology, University of Illinois, Urbana, Ill.

What is claimed is:

1. A method of combatting plant insect pests which comprises applying to the plant environment or plant seed plant-colonizing bacteria having within it chromosome heterologous DNA encoding for the protein toxin of *Bacillus thuringiensis* which bacteria are capable of proliferating in the plant environment and which express an insecticidally effective amount of the protein toxin.
2. The method of claim 1 wherein the amount of plant-colonizing bacteria applied is sufficient to sustain or to propogate to the amount sufficient to express at least 0.5 nanograms of insecticidally active protein per each insect to be controlled.
3. The method of claim 2 wherein the plant-colonizing bacteria expresses 1 to 100 nanograms of insecticidally active protein per each insects to be controlled.
4. The method of claim 3 wherein the heterologous DNA is derived from *Bacillus thuringiensis* subspecies selected from the group consisting of kurstaki, berliner, israelensis, and tenebrionis.
5. The method of claim 4 wherein the heterologous DNA is derived from *Bacillus thuringiensis* subsp. kurstaki.
6. The method of claim 4 wherein the insect pests are selected from the group Lepidoptera, Coleoptera, and Diptera.
7. The method of claim 6 wherein the insect pests are larvae of Lepidoptera.
8. The method of claim 5 wherein the heterologous DNA is from about 4.6 Kb to about 2.4 Kb in size.
9. The method of claim 8 wherein the plant-colonizing bacterium is selected from the genera consisting of Pseudomonas, Agrobacterium, Rhizobium, Erwinia, Azotobacter, Azospirillum, Klebsiella, Alcaligenes and Flavobacterium.
10. The method of claim 9 wherein the plant-colonizing microorganism is from the genus Pseudomonas or Agrobacterium.
11. The method of claim 10 wherein the plant-colonizing microorganism is applied to the plant environment.
12. The method of claim 10 wherein the plant-colonizing microorganism is applied to the plant seed.
13. A method of combatting plant insect pests which comprises applying to the plant environment or plant seed an amount of *Pseudomonas fluorescens* bacteria 3732-3-7A ATCC No. 39912, said *Pseudomonas fluorescens* bacteria being capable of proliferating in the plant environment in an amount sufficient to sustain or to propagate to an amount capable of expressing at least 0.5 nanograms of insecticidally active protein per each insect to be controlled.
14. A method of combatting plant insect pests which comprises applying to the plant environment or plant seed an amount of *Pseudomonas fluorescens* bacteria 112-12A ATCC No. 39913, said *Pseudomonas fluorescens* bacteria being capable of proliferating in the plant environment in an amount sufficient to sustain or to propagate to an amount capable of expressing at least 0.5 nanograms of insecticidally active protein per each insect to be controlled.
15. A method of combatting plant insect pests which comprises applying to the plant environment or plant seed an amount of *Pseudomonas fluorescens* bacteria 112-12C ATCC No. 53279, said *Pseudomonas fluorescens* bacteria being capable of proliferating in the plant environment in an amount sufficient to sustain or to propagate to an amount capable of expressing at least 0.5 nanograms of insecticidally active protein per each insect to be controlled.
16. A method of combatting plant insect pests which comprises applying to the plant environment or plant seed an amount of *Pseudomonas fluorescens* bacteria 112-12D ATCC No. 53280, said *Pseudomonas fluorescens* bacteria being capable of proliferating in the plant environment in an amount sufficient to sustain or to propagate to an amount capable of expressing at least 0.5 nanograms of insecticidally active protein per each insect to be controlled.
17. The method of claim 13 wherein the bacteria expresses 1 to 100 nanograms of insecticidally active protein per each insect to be controlled.
18. The method of claim 1 wherein the insect pests are larvae of Lepidoptera.
19. The method of claim 17 wherein said *Pseudomonas fluorescens* is applied to the plant environment.
20. The method of claim 17 wherein said *Pseudomonas fluorescens* is applied to the plant seed.
21. The method of claim 14 wherein the bacteria expresses 1 to 100 nanograms of insecticidally active protein per each insect to be controlled.
22. The method of claim 21 wherein the insect pests are larvae of Lepidoptera.
23. The method of claim 21 wherein said *Pseudomonas fluorescens* is applied to the plant environment.
24. The method of claim 21 wherein said *Pseudomonas fluorescens* is applied to the plant seed.
25. The method of claim 15 wherein the bacteria expresses 1 to 100 nanograms of insecticidally active protein er each insect to be controlled.

26. The method of claim 25 wherein the insect pests are larvae of Lepidoptera.

27. The method of claim 25 wherein said *Pseudomonas fluorescens* is applied to the plant environment.

28. The method of claim 25 wherein said *Pseudomonas fluorescens* is applied to the plant seed.

29. The method of claim 16 wherein the bacteria expresses 1 to 100 nanograms of insecticidally active protein per each insect to be controlled.

30. The method of claim 29 wherein the insect pest are larvae of Lepidoptera.

31. The method of claim 29 wherein said *Pseudomonas fluorescens* is applied to the plant environment.

32. The method of claim 29 wherein said *Pseudomonas fluorescens* is applied to the plant seed.

* * * * *